(12) United States Patent
Reggelin et al.

(10) Patent No.: US 6,900,322 B1
(45) Date of Patent: May 31, 2005

(54) METHOD FOR STEREOCHEMICALLY CONTROLLED PRODUCTION OF ISOMERICALLY PURE HIGHLY SUBSTITUTED AZACYCLIC COMPOUNDS

(75) Inventors: Michael Reggelin, Hadamar (DE);
Timo Heinrich, Rodenbach (DE);
Bernd Junker, Bad Soden (DE);
Jochen Antel, Bad Muender (DE); Ulf Preuschoff, Uelzen (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 09/700,278

(22) PCT Filed: May 10, 1999

(86) PCT No.: PCT/DE99/01417

§ 371 (c)(1),
(2), (4) Date: Nov. 13, 2000

(87) PCT Pub. No.: WO99/58500

PCT Pub. Date: Nov. 18, 1999

(30) Foreign Application Priority Data

Jul. 13, 1998 (DE) .......................................... 198 21 418

(51) Int. Cl.[7] ..................... C07D 209/36; C07D 209/52; C07D 211/46; C07D 215/233; C07D 221/16

(52) U.S. Cl. ........................ 546/79; 546/138; 546/156; 546/141; 546/183; 546/103; 546/216; 546/221; 548/512; 548/515; 548/556; 548/557; 548/439; 548/452; 548/466

(58) Field of Search .......................... 546/79, 138, 156, 546/141, 183, 103, 216, 221; 548/556, 557, 512, 452, 439, 515

(56) References Cited

U.S. PATENT DOCUMENTS 5,252,747 A * 10/1993 Chu ........................... 548/541

FOREIGN PATENT DOCUMENTS

EP 0 394 991 10/1990
EP 0 558 443 9/1993

OTHER PUBLICATIONS

Greene TW and Wuts PGM. Protective groups in organic synthesis. (1991). John Wiley & Sons, Inc. pp. 12, 68, 309, 318, 327, 313, 379.*
Comins et al., "Regio—and Stereoselective Addition of Nucleophiles to 1–Phenoxycarbonyl–2, 3–Dihydropyridinium Salts", Heterocycles, vol. 37, No. 2, 1994, pp. 1121–1140 (XP–002119392).
Beak et al., "α–Lithiomine Synthetic Equivalents: Syntheses of Diastereoisomers from Boc Derivatives of Cyclic Amines", J. Org. Chem. 1993, 58, 1109–1117 (XP–002119393).

Torii et al., "Facile Access to 6–Methoxy–1, 2, 3, 6–tetrahydro—and 4–Hydroxy–1, 2, 3, 4–tetrahydropyridines by Electrochemical Haloalkoxylation–Dehydrohalogenation Sequence as a Key Operation", Synthesis, Mar. 1987, pp. 242–245 (XP–002119394).
Meleshina et al., "Calculation of the Effect of Substituents on the Vibrational Spectra of α–and β–isomers of 2, 6–dimethyl–4–hydroxy–1, 2, 3, 4–tetrahydroquinolines", Zh. Prikl. Spektrosk, 1974, 21 (2) , pp. 286–90 (XP–002119399).
Schindler et al., "Stereochemistry of the intermediates (aldol bases) of the Doebner–von Miller quinoline synthesis", Helv. Chim. Acta (1970), 53 (4) , pp. 776–779 (XP 002119395).
Reggelin et al., "Metalated 2–Alkenylsulfoximines: Efficient Solutions for Asymmetric d[3]–Synthons", J. Am. Chem. Soc. 118 (1996) pp. 4765–4777 (XP–002119396).
Reggelin et al., "One–Pot Synthesis of (S) –4–Isopropyl–2–p–toluene–4, 5–dihydro–[1,2λ[6],3] oxathiazole 2–Oxides: Efficient Precursors of Optically Active Sulfoximines", Tetrahedron Letters, vol. 33 No. 46 (1992) pp. 6959–6962 (1992) (XP–002119397).
Reggelin et al., "Metalated 2–Alkenylsulfoximines in Asymmetric Synthesis: Diastereoselective Preparation of Highly Substituted Pyrrolidine Derivatives", Angew. Chem. Int. Ed. 37 no. 20 (1998) pp. 2883–2886 (XP–002119398).
Kobayashi et al., "The Asymmetric Diels–Alder Reaction of α,β–Unsaturated Aldehydes with Dienes Using a Chiral Boron Reagent as a Catalyst", Chemistry Letters (1991) pp. 1341–1344.
Williams et al., "Asymmetric [1, 3]–Dipolar Cycloaddition Reactions: Synthesis of Highly Substituted Proline Derivatives", Journal of Organic Chemistry 57 (1992) pp. 6527–6532.
Wehner et al., "Synthese von D–und L–1, 4–Didesoxy–1, 4–iminolyxit durch ($C_2$+ $C_3$)–Nitroaldol–Addition mit 2–o–Benzylglycerinaldehyd", Angewandte Chemie 102 (1990) pp. 1180–1182.

(Continued)

Primary Examiner—Evelyn Mei Huang
(74) Attorney, Agent, or Firm—Crowell & Moring LLP

(57) ABSTRACT

A method for stereochemically controlled production of azacyclic compounds of general formula (I)

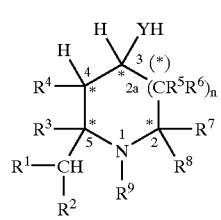

in which the substituents have the meanings given in the specification. The invention also relates to intermediate products of this method and to novel azacyclenes.

13 Claims, No Drawings

OTHER PUBLICATIONS

Laschat et al., "Enantioselective Approach Towards Potential Substance P Antagonists via Hetero–Ene Reaction of Phenylglycine Derivatives", Synthesis (Apr. 1997) pp. 475–479.

Kuzmitskii et al., "Relation between structure and central nicotinic choline–blocking action in a series of stereoisomeric 2, 4, 7–and 2, 4, 9–substituted decahydroquinolines and their N–methyl analogs", Chemical Abstracts vol. 91:117158c (1979) pp. 18–19.

Lash et al., An Improved Synthesis of Pyrroles from N–p–Toluenesulfonylglycine Esters and α,β–Unsaturated Aldehydes and Ketones [1], Journal of Heterocyclic Chemistry, vol. 28 (Nov. 1991) 1671–1676.

Reggelin et al., "Metallated 2–Alkenyl Sulfoximines in Asymmetric Synthesis: Regio—and Stereoselective Synthesis of Highly Substituted Tetrahydrofurans", Liebigs Annalen der Chemie/RECUEIL (1997) pp. 1881–86.

Bolte, "(+)–(2S, 3S, 4S, 5S)–2–Benzyl–N–(tert–butyloxycarbonyl)–3–hydrox at 143 K", Acta Crystallographica Section C, electronically published paper QA0017 {=(IUCr) Acta C Paper QA 0017 (www.iucr.ac.uk).

Dess et al., "A Useful 12–I–5 Triacetoxperiodinane (the Dess–Martin Periodinane) for the Selective Oxidation of Primary or Secondary Alcohols and a Variety of Related 12–I–5 Species", J. Am. Chem. Soc., vol. 113, No. 19 (1991) pp. 7277–7287.

Dess et al., "Readily Accessible 12–I–5 Oxidant for the Conversion of primary and Secondary Alcohols to Aldehydes and Ketones", J. Org. Chem. 48 (1983) pp. 4155–4156.

The ChiroChem™ Collection, Series 1, FMOC unnatural amino acids for medicinal and combinatorial chemists, SCRIP No. 2311, Feb. 1998, p. 15.

Seebach et al., "β–Peptides: Synthesis by *Arndt–Eister*Homologation with Concimitant Peptide Coupling. Structure Determination by NMR and CD Spectroscopy and by X–Ray Crystallography. Helical Secondary Struture of a β–Hexapeptide in Solution and Its Stability towards Pepsin", Helvetica Chimica Acta vol. 79 (1996) pp. 913–941.

Seebach et al., "Probing the Helical Secondary Structure of Short–Chain β–Peptides", Helvetica Chimica Acta vol. 79 (1996) pp. 2043–2066.

M. Bolte, "(2S, 3R, 4R, 5R, SS)–2–Benzyl–3–hydroxy–5–{N–[(S)–1–hydroxy–3–n at 140 K", Acta crystallographica Section C, electronically published paper QA0019 {=(IUCr) Acta C Paper QA0019 (www.iucr.ac.uk).

Mitsunobu, "The Use of Diethyl Azodicarboxylate and Triphenylphosphine in Synthesis and Transformation of Natural Products", Synthesis, Jan. 1991, pp. 1–28.

Reggelin et al., "New Stereocontrolled Synthesis of Cyclic Sulfonimidates", Tetrahedron Letters, vol. 36, No. 33 (1995), pp. 5885–5886.

Hintermann et al., "Synthesis of a β–Hexapeptide from (R)–2–Aminomethyl–alkanoic Acids and Structural Investigations", Synlett (May 1997), p. 437.

* cited by examiner

METHOD FOR STEREOCHEMICALLY CONTROLLED PRODUCTION OF ISOMERICALLY PURE HIGHLY SUBSTITUTED AZACYCLIC COMPOUNDS

BACKGROUND OF THE INVENTION

The present invention relates to a novel process for the stereochemically controlled production of novel and known highly substituted azacyclic compounds and to novel intermediate products of this process. Furthermore, the invention relates to novel highly substituted azacyclic compounds which can be built up in isomerically pure manner and which have useful properties for numerous fields of application.

Highly substituted stereoisomers of azacyclic compounds, in particular highly substituted derivatives of pyrrolidines or piperidines, are useful starting materials for numerous applications, and are used, for example, as constituents of chiral catalysts in asymmetrical synthesis (see, e.g., Kobayashi et al., Chemistry Letters (=Chem. Lett.) (1991) 1341–1344), as constituents of biologically active alkaloids (see, e.g., Williams et al., Journal of Organic Chemistry (=JOC) 57 (1992) 6527–6532 and references cited therein; Jäger et al., Angewandte Chemie 102 (1990) 1180–1182) and as constituents of pharmacologically interesting compounds (see, e.g., Laschat et al., Synthesis 4 (1997) 475479). Furthermore, for example decahydroquinolines and pyrrolidines which can be produced according to the process of the invention or ones which are structurally closely related have interesting physiological effects (see, e.g., Kuzmitskii et al., Vestsi Akad. Navuk BSSR, Ser. Khim. Navuk 3 (1979) 82–85/Chemical Abstracts No. 91:117158c; Lash et al., Journal of Heterocyclic Chemistry 28 (1991) 1671–1676). The use of some of the pyrrolidines mentioned above for the production of porphyrin ring systems is also discussed therein. Processes for the production of such azacyclic compounds are also known in part from the literature sources quoted. Certain enantiomers of these compounds may be obtained according to the methods referred to therein usually by means of conventional racemate separation. However, production processes which are not in accordance with the invention are also mentioned, according to which selected individual compounds of substituted azacyclic compounds can be produced in isomerically pure manner. A general process for the stereo-controlled synthesis of isomerically pure, highly substituted azacyclic compounds is not known from the above literature sources.

Furthermore, the stereo-controlled synthesis of some tetrahydrofuran derivatives by reaction of 2-alkenyl sulfoximides with 2-tert. butyldimethyl-silyloxy-propanal (=TBS lactaldehyde) and subsequent fluoride-induced cyclisation is already known (see Reggelin et al., JACS 118 (1996) 4765–4777; Reggelin et al., Liebigs Annalen der Chemie/RECUEIL (1997) 1881–1886). However, highly substituted azacyclic compounds cannot be produced according to the process described therein.

The compound (2S,3S,4S,5S)-(N-tert.-butyloxycarbonyl)-2-benzyl-4,5-dimethyl-3-hydroxypyrrolidine is already known from the Internet publication at the address "www.iucr.ac.uk" by M. Bolte, Acta Crystallographica Section C, electronically published paper QA0017 [=(IUCr) Acta C Paper QA 0017]. The production of this compound is not described in the publication cited.

SUMMARY OF THE INVENTION

It was an object of the present invention to provide a process for the stereochemically controlled production of novel and known highly substituted azacyclic compounds with which the type and number of substituents in these compounds can also be varied widely and which can be built up in isomerically pure manner. Furthermore, it was an object of the invention to provide novel, in particular isomerically pure, highly substituted azacyclic compounds for numerous fields of application.

It has now surprisingly been discovered that highly substituted azacyclic compounds in which the type and number of substituents can be varied widely can be built up in a good yield in particular in isomerically pure manner if metalated 2-alkenyl sulfoximide compounds are reacted according to a process of the invention with N-protected α- or β-aminoaldehydes which may have the substitution pattern given in the description in the α and/or β position.

The subject of the invention is thus a process for the stereochemically controlled production of compounds of the general formula 1,

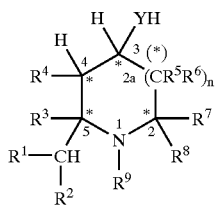

wherein
n is 0 or 1
$R^1$ is hydrogen; $C_1$–$C_6$-alkyl; or phenyl-$C_1$–$C_6$-alkyl optionally substituted one or more times in the phenyl ring by lower alkyl, lower haloalkyl, lower alkoxy or lower haloalkoxy, and
$R^2$ is hydrogen, or
$R^1$ and $R^2$ together are a double-bonded methylene group which may be substituted by $C_1$–$C_5$-alkyl or by phenyl-$C_1$–$C_5$-alkyl optionally substituted one or more times in the phenyl ring by lower alkyl, lower haloalkyl, lower alkoxy or lower haloalkoxy,
$R^3$ is hydrogen, and
$R^4$ is hydrogen; lower alkyl; or phenyl-lower alkyl optionally substituted one or more times in the phenyl ring by lower alkyl, lower haloalkyl, lower alkoxy or lower haloalkoxy, or
$R^3$ and $R^4$ also together are a $C_2$-alkylene chain; or a $C_3$–$C_6$-alkylene chain optionally containing 1 to 3 double bonds, which may be bridged by $C_1$–$C_2$-alkylene which is optionally substituted one or two times by lower alkyl,
$R^5$ is hydrogen; lower alkyl; hydroxy; lower alkoxy; phenyl-lower alkoxy or phenyl-lower alkyl each of which may be optionally substituted one or more times in the phenyl ring by lower alkyl, lower haloalkyl, lower alkoxy or lower haloalkoxy, and
$R^6$ is hydrogen, and
$R^7$ is hydrogen, and
$R^8$ is hydrogen; cyano; optionally esterified carboxy; carbonylamino optionally substituted one or two times at the nitrogen; a monocyclic or bicyclic ring system with 3 to 10 ring carbon atoms which is optionally unsaturated one or more times, the ring carbon atoms of which may be replaced one or more times by nitrogen, oxygen and/or sulfur and which ring system may be substituted one or more times by lower alkyl, lower haloalkyl, lower alkoxy, hydroxy, halogen or by a lower alkylene chain which is bonded to two oxygen atoms bonded to adjacent carbon atoms of the ring system, or also may stand for straight-chain or branched $C_1$–$C_{12}$-alkyl optionally containing one or more double bonds which may be substituted one or more times by halogen, hydroxy, lower alkoxy, optionally esterified carboxy, cyano, mercapto, lower alkylthio, amino, lower alkylamino, carbonylamino optionally substituted one or two times at the nitrogen, a monocyclic or bicyclic ring system with 3 to 10 ring carbon atoms which is optionally unsaturated one or more times, the ring carbon atoms of which may be replaced one or more times by nitrogen, oxygen and/or sulfur and which ring system may be substituted one or more times by lower alkyl, lower haloalkyl, lower alkoxy, hydroxy, halogen or by a lower alkylene chain which is bonded to two oxygen atoms bonded to adjacent carbon atoms of the ring system, or $R^5$ and $R^8$ also, together with the carbon atoms to which they are bonded, may form a monocyclic or bicyclic ring system with 5 to 10 ring carbon atoms which optionally contains 1 to 3 double bonds, the carbon atoms of which which do not bear the substituents $R^5$ or $R^8$ may be replaced one or more times by sulfur, oxygen and/or nitrogen, and which optionally may be substituted one or more times by lower alkyl, lower haloalkyl, lower alkoxy, lower haloalkoxy, hydroxy, halogen or by a lower alkylene chain which is bonded to two oxygen atoms bonded to adjacent carbon atoms of the ring system, or $R^6$ and $R^7$ also together may form a bond, and $R^5$ and $R^8$, together with the carbon atoms to which they are bonded, may form an aromatic $C_6$-ring system which may be fused with 2 to 4 further carbon atoms to form a bicyclic ring system having a total of 3 to 5 double bonds which contains a total of 8 to 10 ring carbon atoms, wherein the carbon atoms of this $C_6$- to $C_{10}$-ring system which do not bear the substituents $R^5$ and $R^6$ may be replaced one or more times by sulfur, oxygen and/or nitrogen, and wherein this $C_6$- to $C_{10}$-ring system may optionally be substituted one or more times by lower alkyl, lower haloalkyl, lower alkoxy, lower haloalkoxy, hydroxy, halogen or by a lower alkylene chain which is bonded to two oxygen atoms bonded to adjacent carbon atoms of the ring system, $R^9$ is hydrogen; lower alkyl; phenyl-lower alkyl optionally substituted one or more times in the phenyl ring by lower alkyl, lower haloalkyl, lower alkoxy or lower haloalkoxy; or an amino protecting group, or $R^8$ and $R^9$ also together may form a $C_3$–$C_4$-alkylene chain, and Y is oxygen or NH, and their acid addition salts, wherein any reactive groups which may be present may be blocked in compounds of Formula I by suitable protecting groups, characterized in that a) a compound of the general formula II,

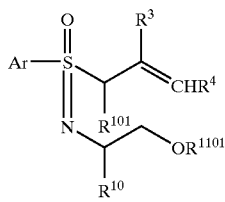

II wherein $R^3$ and $R^4$ have the above meanings, $R^{101}$ has the meaning given above for $R^1$ with the exception of an optionally substituted methylene group, Ar stands for phenyl optionally substituted one or more times by lower alkyl, $R^{10}$ is lower alkyl, or phenyl optionally substituted once in the phenyl ring by lower alkyl or by hydroxy protected with a suitable protecting group, or phenyl-lower alkyl optionally substituted once in the phenyl ring by lower alkyl, and $R^{1101}$ stands for a silyl protecting group, is reacted in succession with a base suitable for the deprotonation thereof, an organometallic reagent of the general formula VII,

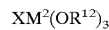

XM²(OR¹²)₃    VII wherein X stands for halogen, $M^2$ is a tetravalent transition metal and $R^{12}$ stands for lower alkyl, phenyl or phenyl-lower alkyl, and a stereoisomer of a compound of the general formula VIII,

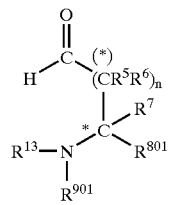

VIII wherein $R^5$, $R^6$, $R^7$ and n have the above meanings, $R^{801}$ has the meaning of $R^6$, with any reactive groups if necessary being blocked by base-stable protecting groups, $R^{901}$ stands for hydrogen or together with $R^{801}$ stands for a $C_3$–$C_4$-alkylene chain and $R^{13}$ is an amino protecting group which when cleaved leaves behind a nitrogen nucleophile, to form a stereoisomer of a compound of the general formula IX,

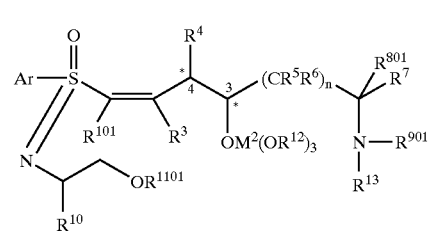

IX wherein $R^{101}$, $R^3$, $R^4$, $R^5$, $R^8$, $R^7$, $R^{801}$, $R^{901}$, $R^{10}$, $R^{1101}$, $R^{12}$, $R^{13}$, n, Ar and $M^2$ have the above meanings, b) the resulting compound of Formula IX is converted, by treatment with a reagent suitable for removing the group $R^{13}$, into a compound of the general formula Xa,

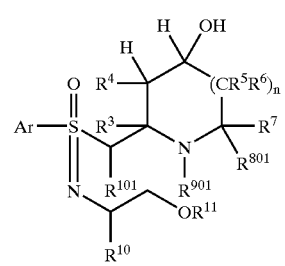

Xa wherein $R^{101}$, $R^3$, $R^4$, $R^5$, $R^6$, $R^7$, $R^{801}$, $R^{901}$, $R^{10}$, n and Ar have the above meanings and $R^{11}$ stands for hydrogen or a silyl protecting group and, if $R^{901}$ stands for hydrogen, the nitrogen atom in the cyclic parent structure of the resulting compound of Formula Xa is blocked with a base-stable protecting group and any silyl protecting group $R^{11}$ which may still be present is cleaved off, and c) for the production of a compound of the general formula Ia,

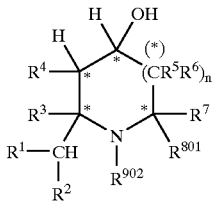

Ia wherein $R^1$, $R^2$, $R^3$, $R^4$, $R^5$, $R^6$, $R^7$, $R^{801}$ and n have the above meanings and $R^{902}$ stands for a base-stable protecting group or, together with $R^{801'}$, for a $C_3$–$C_4$-alkylene chain, ca) a resulting compound of Formula Xa or a compound produced by cleaving off the silyl protecting group $R^{11}$ is reacted with a reagent suitable for the reductive cleavage of the sulfonimidoyl-alkyl bond, in order to obtain a compound of the general formula Ib,

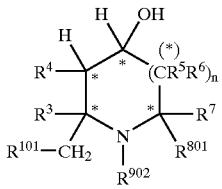

Ib wherein $R^{101}$, $R^3$, $R^4$, $R^5$, $R^6$, $R^7$, $R^{801}$, $R^{902}$ and n have the above meanings, or cb) in a resulting compound of Formula Xa wherein $R^{101}$ does not stand for hydrogen, the sulfonimidoyl-alkyl bond is cleaved after electrophilic activation of the sulfonimidoyl unit under the conditions of a base-induced elimination, in order to obtain a compound of the general formula Ic,

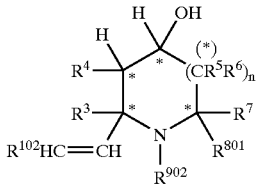

Ic wherein $R^3$, $R^4$, $R^5$, $R^6$, $R^7$, $R^{801}$, $R^{902}$ and n have the above meanings and $R^{102}$ stands for $C_1$–$C_5$-alkyl; or phenyl-lower alkyl optionally substituted one or more times in the phenyl ring by lower alkyl, lower haloalkyl, lower alkoxy or lower haloalkoxy, the lower alkylene chain of which phenyl-lower alkyl may contain 1 to 5 carbon atoms, and a resulting compound of Formula Ia is reacted if desired one or more times by reaction, in each case with inversion of the configuration at the ring carbon atom in the 3-position of the compounds of Formula Ia, with a nucleophilic reagent suitable for regenerating an OH group or for generating an $NH_2$ group in the 3-position, and/or if desired any protecting groups are cleaved again in compounds of Formula Ia and if desired the optionally released NH group in the 1-position of the cyclic parent structure is reacted with a reagent capable of N-alkylation or one capable of amide formation or is blocked with an amino protecting group, in order to obtain compounds of Formula I, and free compounds of Formula I if desired are reacted to form acid addition salts, or acid addition salts of compounds of Formula I are reacted to form free compounds. Furthermore, the subject of the invention is novel azacyclic compounds.

DETAILED DESCRIPTION OF PREFERRED EMBODIMENTS

If substituents in compounds of Formula I or in other compounds described within the scope of the present invention are or contain lower alkyl, this may be branched or unbranched, and usually contain 1 to 4 carbon atoms.

If substituent constituents, for example radicals bonded to phenyl rings, may be contained one or more times in the definitions of the substituents of compounds of Formula I or of Formula X, these may usually be contained one to three times. If one or more carbon atoms may be replaced by heteroatoms such as oxygen, sulfur or nitrogen in compounds of the present invention, usually one to three carbon atoms may be replaced by heteroatoms. Preferably one carbon atom may be replaced by a heteroatom. If substituents may contain one or more double bonds, cyclic substituents, depending on ring size, may usually contain 1–4 double bonds and may preferably form aromatic systems. Aliphatic substituents may, for example, contain 1 to 3 double bonds, depending on chain length.

Preferably, compounds of Formula Ia may be produced wherein the substituents $R^1$ and $R^2$ each stand for hydrogen. Particularly preferably, compounds of the general formula Ib may be produced, in particular when the substituent $R^{101}$ is hydrogen.

The substituent $R^3$ may preferably stand for hydrogen, or, together with $R^4$, may form an optionally bridged $C_3$–$C_6$-alkylene chain. Preferably those compounds of Formula I wherein $R^4$ is not hydrogen, but, for example, lower alkyl, may be produced in isomerically pure manner. If $R^4$ has a meaning other than hydrogen, the ring closure reaction to form compounds of Formula Xa in process step b) takes place with particularly high selectivity, and the compounds of Formula Ia and of Formula I obtained from the compounds of Formula Xa may be obtained with a particularly low proportion of byproducts. If $R^3$ and $R^4$ together stand for an optionally bridged $C_3$–$C_6$-alkylene chain, the alkylene chain may preferably contain 3 to 4 carbon atoms. If the alkylene chain is bridged, the bridging chain may preferably have 1 carbon atom, which may preferably be substituted by di-lower alkyl. In particular, $R^3$ and $R^4$, together with the carbon atoms to which they are bonded, may form the 7,7-dimethylbicyclo[3.1.1]heptane system.

If the substituent $R^8$ is or contains optionally esterified carboxy, the carboxyl group may be esterified with conventional, non-sterically-hindered alcohols, for example with cycloaliphatic or straight-chain or branched aliphatic $C_1$–$C_8$-alcohols optionally containing one or more double bonds, which alcohols may optionally be substituted one or more times by halogen or lower alkoxy, or alternatively with phenyl-lower alkyl alcohols optionally substituted one or more times in the phenyl ring by lower alkyl, lower haloalkyl, lower alkoxy or lower haloalkoxy. If $R^8$ is or contains carbonylamino optionally substituted one or two times at the nitrogen, the amino group contained therein may for example be substituted once by $C_3$–$C_8$-cycloalkyl-lower alkanoyl or straight-chain or branched aliphatic $C_1$–$C_8$-alkanoyl, each of which may optionally be substituted one or more times by halogen or lower alkoxy, or the amino group may be substituted once by phenyl-lower alkanoyl optionally substituted one or more times in the phenyl ring by lower alkyl, lower haloalkyl, lower alkoxy or lower haloalkoxy, or the amino group may for example also be substituted one or two times by $C_3$–$C_8$-cycloalkyl-lower alkyl or straight-chain or branched aliphatic $C_1$–$C_8$-alkyl, each of which optionally may be substituted one or more times by halogen or lower alkoxy; phenyl-lower alkyl optionally substituted one or more times in the phenyl ring by lower alkyl, lower haloalkyl, lower alkoxy or lower haloalkoxy; or the amino group may for example be protected with a suitable amino protecting group. If $R^8$ is or contains an optionally substituted monocyclic or bicyclic ring system with 3 to 10 ring carbon atoms, this may for example stand for cyclopropyl, cyclopentyl, cyclohexyl, phenyl, p-bromophenyl or 3-indolyl.

Examples of compounds of Formula I, Ia, Ib and/or Ic according to the invention which can be produced without difficulty using the process according to the invention have as substituents $R^8$ or $R^{801}$ hydrogen, lower alkyl, phenyl, lower-alkyl phenyl or lower-alkyloxy lower alkyl, or for example also contain a fused aromatic bring formed from $R^8$, or $R^{801}$, $R^5$, $R^6$ and $R^7$. Likewise, compounds of Formula I, Ia, Ib and/or Ic in which $R^{801}$ together with $R^{901}$ forms a $C_3$–$C_4$-alkylene chain can be produced without difficulty.

Suitable protecting groups which can be used in the compounds given in the context of the present invention are known, for example from McOmie, "Protective Groups in Organic Chemistry", Plenum Press, or from Green, Wuts, "Protective Groups in Organic Synthesis", Wiley Interscience Publication.

The deprotonation of compounds of Formula II with suitable bases and the reaction of the deprotonated compounds of Formula II with organometallic reagents of Formula VII and then with the aminoaldehydes of Formula VII to form the compounds of Formula IX in process step a) can be carried out in a polar or weakly polar aprotic solvent which is inert under the reaction conditions, for example in cyclic or open-chained lower-alkyl ethers such as diethyl ether (=ether) or tetrahydrofuran (=THF), in low-molecular polyethylene glycol ethers such as diethylene dimethyl ether (=diglyme) or in substituted benzenes such as toluene or xylene. Preferably, weakly polar solvents such as substituted benzenes, in particular toluene, may be used. If toluene is used as solvent, particularly good yields of the products of Formula IX or of the products of Formula Xa obtained therefrom are obtained. Advantageously, the reaction can be performed as a one-pot reaction, by deprotonating a preferably isomerically pure 2-alkenyl sulfoximide of Formula II in a suitable solvent as named above at low temperature, for example between −100° C. and −50° C., preferably at −78° C., for about 5 to 30 minutes with a suitable base, transmetalating the deprotonated form of the compound of Formula II at slightly elevated temperature, for example between −20° C. and 10° C., preferably at 0° C., with an organometallic reagent of Formula VII, and then, again at low temperature, for example between −100° C. and −50° C., preferably at −78° C., reacting the resulting intermediate product with an N-protected aminoaldehyde of Formula VII. Suitable bases for deprotonating compounds of Formula II are preferably lithiated lower alkyl compounds such as n-butyllithium. Usually, the base may be used in a slight excess, for example in a molar ratio of about 1:1.05 to about 1:1.20, relative to the quantity of the compound of Formula II used. In organometallic reagents of Formula VII, X may stand for halogen, preferably for chlorine. Zirconium, for example, but preferably titanium, may be used as the tetravalent transition metal $M^2$. Suitable substituents $R^{12}$ are, for example, branched and unbranched lower alkyl groups, preferably isopropyl. Particularly preferably, chlorotris(isopropoxy)titanium may be used as the compound of Formula VII. The organometallic reagent is advantageously used in a slight excess, for example in a molar ratio of about 1.1:1 to 1.3:1, relative to the quantity of the compound of Formula II which is used.

The compounds of Formula VIII represent protected chiral α- or β-aminoaldehydes, and may preferably be used in isomerically pure form. Suitable protecting groups $R^{13}$ which when cleaved produce a nucleophilic nitrogen atom in compounds of Formula VIII are preferably base-labile protecting groups. Particularly preferably, the fluoren-9-yl-methyloxycarbonyl protecting group (=FMOC) may be used as group $R^{13}$. The cleaving of the protecting group $R^{13}$ and the ring closure reaction may preferably take place in a single reaction step, provided that FMOC is used as protecting group.

In the starting compounds of Formula VIII, the substituent $R^{801}$ has the meaning given for $R^8$, but if need be reactive groups contained in the substituent $R^8$, for example hydroxy, amino, mercapto or carboxy, are each blocked by known base-stable protecting groups, for example protecting groups stable against non-nucleophilic or weakly nucleophilic bases such as pyridine, in order to avoid unwanted side-effects. Isomerically pure aminoaldehydes of Formula VIII are known, or can be produced from known compounds in known manner. Thus, for example, the aldehydes of Formula VIII can be obtained by known mild oxidation processes from the primary alcohols corresponding to the aldehydes. Suitable mild oxidation processes are those processes which do not cause racemisation of the chiral centres in compounds of Formula VIII, for example the oxidation with activated oxalyl chloride (=Swem oxidation) or alternatively oxidation with 1,1,1-triacetoxy-1,1-dihydro-1,2-benziodoxol-3(1H)-one (=periodinane; Dess-Martin oxidation, see, e.g. J. C. Martin et al., JACS 113 (1991), 7277–7287; D. B. Dess, J. C. Martin, Journal of Organic Chemistry 48 (1983), 4155–4156). If the oxidation takes place in accordance with the Dess-Martin method referred to above, an aminoaldehyde of Formula VIII can be produced according to a process mentioned in the above literature, or a process analogous thereto. For example, a primary alcohol suitable as precursor for an aldehyde of Formula VIII in a dipolar-aprotic solvent, for example in a halogenated lower alkane such as dichloromethane, may be reacted with a slight excess of the triacetoxy periodinane, for example in a molar ratio of about 1.2:1 to about 1.4:1, relative to the compound of Formula VIII which is used. The reaction can be carried out at temperatures between −20° C. and room temperature, preferably at 0° C.

The primary alcohols corresponding to the aldehydes of Formula VIII are known or can be produced from known precursor compounds by known processes. For example, the primary alcohols may be produced by known reduction processes, for example by reduction with complex alkali metal hydrides such as lithium aluminium hydride, from the corresponding free aminocarboxylic acid precursor compounds. Preferably aminocarboxylic acids which are already present in isomerically pure, for example enantiomerically pure, form, such as the known, naturally occurring 20 proteinogenic α-amino acids, are suitable. Likewise, commercially available unnatural isomerically pure α-amino acids obtainable, for example, from the company ChiroTech, Cambridge (catalogue "The ChiroChem™ Collection, Series 1, FMOC unnatural amino acids for medicinal and combinatorial chemists", SCRIP No. 2311/20.02.1998, page 15), can be used. For the production of compounds of Formula I wherein n=1, the point of departure may expediently be isomerically pure β-amino acids known per se, for example from Nohira et al, Bulletin of the Chemical Society of Japan 43 (1970) 2230 ff. Furthermore, isomerically pure β-amino acids suitable for the invention can also be produced from isomerically pure α-amino acids by homologisation, for example homologisation according to Amdt-Eistert in accordance with the methods of D. Seebach et al., Helvetica Chimica Acta (=HCA) 79 (1996) 913–941; 2043 ff. and Synlett (1997) 437 ff. α-chiral, β-amino acids wherein $R^5$ has a meaning other than hydrogen can be obtained in known manner, for example by asymmetrical alkylation of chiral oxazolidinones with chloromethyl amides in accordance with the method of D. Seebach et al., Synlett (1997) 437 ff., or alternatively in accordance with other known methods.

The desired protecting groups $R^{13}$ can be introduced into compounds of Formula VIII or the precursor compounds thereof mentioned above using known methods.

In process step a), two new stereogenic carbon atoms are produced in the vinyl sulfoximides of Formula IX by the reaction between a chiral aminoaldehyde of Formula VIII and the chiral intermediate product resulting from a 2-alkenyl sulfoximide of Formula II by deprotonation and transmetalation. These new stereogenic carbon atoms are the atoms C-3 and C-4 in compounds of Formula IX. The substituents $R^4$ on C-4 and $OM^2(OR^{12})_3$ on C-3 as a rule adopt an "anti" orientation to each other with high selectivity of at least 95% upon the formation of the vinyl sulfoximides of Formula IX according to the process of the invention. The absolute configurations at the newly produced chiral centres C-3 and C-4 are then controlled during the reaction in each case by the absolute configuration at the sulfur atom in compounds of Formula II in the manner of a regio- and diastereo-controlled reaction. If the sulfur atom in compounds of Formula II is in the R configuration, the prochiral carbonyl group in the aldehydes of Formula VIII will be attacked from the Si side. If, on the other hand, the sulfur atom in compounds of Formula II is in the S configuration, the prochiral carbonyl group in the aldehydes of Formula VIII will be attacked from the Re side. Owing to the absolute configuration of the compounds of Formula IX which is established in this manner, the stereochemistry of the compounds of Formulae Ia, Ib and Ic is also established at the corresponding chiral centres as a "cis" orientation. The absolute configuration at the chiral carbon atom of an aminoaldehyde of Formula VIII scarcely has any influence on the stereochemistry on the carbon atoms C-3 and C-4 of the compounds of Formula IX.

The treatment of compounds of Formula IX with a reagent suitable for cleaving the protecting group $R^{13}$ in process step b) in order to obtain compounds of Formula Xa can be effected immediately following process step a) in situ in known manner, without isolation of the compounds of Formula IX being necessary. Accordingly, the reaction can be performed in solvents stated above and at temperatures given above between −100° C. and −50° C., preferably at −78° C. Base-labile protecting groups may, for example, be cleaved with known non-nucleophilic or weakly nucleophilic organic bases which are soluble in the reaction mixture. If the FMOC group is used as amino protecting group $R^{13}$, piperidine is preferred as a base for the cleavage thereof. Usually the base is used in a hyperstoichiometric quantity, for example in a molar ratio of about 5:1 to about 15:1, preferably of about 10:1, relative to the quantity of compounds of Formula IX resulting from compounds of Formula II which is used. Once addition of the base has taken place, first of all thawing to 0° C. and later to room temperature can be effected, and the reaction mixture can be worked up in conventional manner, in which case optionally resulting byproducts can be separated in known manner, for example by crystallisation and/or chromatography.

Due to the cleaving of the amino protecting group $R^{13}$ from compounds of Formula IX, preferably due to the base-induced cleaving thereof, a ring closure reaction to form compounds of Formula Xa is initiated. In particular for compounds of Formula IX in which $R^4$ is not hydrogen, the cyclisation reaction takes place such that the sulfonimidoyl radical in the 5-position of the resulting compound of Formula Xa preferentially adopts the "trans" position to the hydroxyl group in the 3-position of the resulting ring skeleton.

In resulting azacyclic compounds which contain a secondary ring nitrogen atom, this nitrogen atom can then be further reacted in known manner with a compound which contains a group suitable for reaction with a secondary amine. For example, a reaction of the nitrogen atom with known carboxylic acids to form peptide bonds can take place. Likewise, the above nitrogen atom can also be alkylated in known manner, for example by reacting with an alkyl halide such as a phenyl-lower alkyl halide, for example benzyl chloride. Using these methods described above, or in another known manner, the nitrogen atom may also be blocked with a conventional amino protecting group, preferably a base-stable protecting group. In particular, it is advantageous to block the ring nitrogen atom in compounds of Formula Xa with a base-stable protecting group if compounds of Formula Ib are to be produced. Suitable base-stable protecting groups are preferably protecting groups which form a carbamate, in particular the tert. butyloxycarbonyl protecting group (=BOC).

Any protecting groups can if desired also be cleaved off again in known manner, optionally selectively, from compounds of Formula Xa. For example, it may in particular be advantageous to cleave off a silyl protecting group $R^{11}$ which may possibly still be present after process step b) from compounds of Formula Xa before reaction with a reagent suitable for reductive cleavage of the sulfonimidoyl-alkyl bond in process step ca) in known manner, provided that this cleavage of the silyl protecting group has not taken place spontaneously in process step b). An example of a silyl protecting group which is usually spontaneously cleaved off in process step b) without requiring additional treatment is trimethylsilyl (=TMS).

Compounds of Formula Xa or compounds obtainable from compounds of Formula Xa by cleaving off protecting groups are novel compounds having useful properties, and may, for example, serve as intermediate products for the production of compounds of Formula I. (2S,3R,4R,5R,$S_S$)-2-benzyl-3-hydroxy-5-{N-[(S)1-hydroxy-3-methylbut-2-yl]-4-methylphenylsulfonimidoylmethyl}-4-methyl-1-(4-methylphenylsulfonyl)pyrrolidine is already known from the Internet publication at the address "www.iucr.ac.uk" by M. Bolte, Acta Crystallographica Section C, electronically published paper QA0019[=(IUCr) Acta C Paper QA0019]. However, no process for the production of this compound is mentioned in the publication cited.

The reductive cleavage of the sulfonimidoyl-alkyl bond in a resulting compound of Formula Xa or in a compound obtained from a compound of Formula Xa by the reactions at the ring nitrogen atom described above in process step ca) for the production of compounds of Formula Ib can be performed in a polar or weakly polar solvent given above for the reaction of compounds of Formula II with compounds of Formula VII or in mixtures of these solvents. Preferably THF may be used. The reaction can be performed at temperatures between −20° C. and room temperature, preferably at 0° C. Suitable reagents for cleaving the sulfonimidoyl-alkyl bond are, for example, reducing agents such as Raney nickel, lithium naphthalenide or samarium (II) iodide. Preferably samarium (II) iodide may be used.

If the desulfurisation is performed with samarium (II) iodide, this can be produced in known manner in situ from samarium and diiodomethane. Usually the samarium (II) iodide is then used in a hyperstoichiometric quantity, for example in a molar ratio of about 3:1 to about 7:1, relative to the compound of Formula Xa used. To perform the reaction, a proton source, such as a protic compound soluble in the solvent used, is added in a suitable quantity to the reaction mixture consisting of compound of Formula Xa and samarium diiodide. A lower alcohol such as methanol, for example, may be used as proton source. Preferably anhydrous methanol is used. A suitable quantity of the proton source may, for example, be between 2 and 5 equivalents, relative to one equivalent of the quantity of sulfur contained in a compound of Formula Xa. Compounds of Formula Xa in which a secondary ring nitrogen atom is blocked by a carbamate protecting group, preferably the BOC protecting group, can be used particularly advantageously in this case.

The cleavage of the sulfonimidoyl-alkyl bond under the conditions of a base-induced reductive elimination in a resulting compound of Formula Xa wherein $R^{101}$ is not hydrogen, or in a compound obtained from a compound of Formula Xa by the reactions at the ring nitrogen atom described above in process step ca) for the production of compounds of Formula Ic can be carried out in a polar or weakly polar solvent given above for the reaction of compounds of Formula II with compounds of Formula VII, or alternatively in a partially halogenated lower-alkyl solvent such as dichloromethane. Preferably dichloromethane may be used. Suitable bases for cleaving the sulfonimidoyl-alkyl bond by β-elimination are non-nucleophilic organic bases such as bicyclic amidines, for example 1,5-diazabicyclo [4.3.0]-5-nonene (=DBN) or 1,8-diazabicyclo[5.4.0]-7-undecene (=DBU). Preferably DBU may be used. Expediently, the reaction is performed such that the sulfonimidoyl group of a compound of Formula Xa given above is electrophilically activated in known manner. To this end, the compound of Formula Xa may be reacted at temperatures between −25° C. and −15° C. with a compound suitable for forming a good leaving group from the sulfonyl group, or with a lower-alkyl oxonium tetrafluoroborate such as trimethyloxonium tetrafluoroborate, known as "Meerwein salt". Reagents which are capable of forming a good leaving group by attacking the sulfonyl group are, for example, esters or halides of sulfonic acids such as methanesulfonic acid chloride, trifluoromethanesulfonic acid chloride, trifluoromethanesulfonic acid methyl ester (=methyl triflate) or trifluoro-methanesulfonic acid trimethylsilyl ester (=TMS triflate). Preferably methyl triflate may be used. Usually, the resulting reaction mixture is allowed to thaw to room temperature once reaction has taken place, and then the above-mentioned base is added.

In the resulting compounds of Formula Ia, the relative orientation of the sulfonimidoyl substituent in the 5-position and of the hydroxyl group in the 3-position resulting in process step b) by ring closure to form compounds of Formula Xa is established as a "trans" orientation to each other. Compounds of Formula I wherein the substituent YH in the 3-position may be hydroxy or amino and/or wherein the substituents YH in the 3-position and $R^1$—CHR$^2$— in the 5-position may also be in the "cis" orientation to each other may be obtained if desired from compounds of Formula Ia by a nucleophilic substitution reaction at the ring carbon atom in the 3-position performed one or more times and taking place with inversion; Such nucleophilic substitution reactions are known per se and may be performed, for example, under the conditions of a Mitsunobu reaction (see e.g. Mitsunobu, Synthesis 1 (1981) 1–28).

If, for example, compounds of Formula I wherein YH stands for hydroxy and wherein the substituents OH in the 3-position and $R^1$—CHR$^2$— in the 5-position are in a "cis" orientation to each other are desired, expediently a Mitsunobu reaction can be performed in that a solution of a compound of Formula Ia, wherein if necessary any additional hydroxyl groups present are blocked by protecting groups, and of triphenylphosphine in an organic solvent which is inert under the reaction conditions, such as a cyclic or open-chained lower-alkyl ether, for example diethyl ether or THF, are added to a receiving solution consisting of a solution of diethyl azodicarboxylate (=DEAD) and an acid, for example phosphoric acid or a carboxylic acid such as benzoic acid. The reaction can preferably be performed at room temperature. The ester of a desired compound of Formula I obtained in this manner may if desired then be cleaved in known manner, in order to obtain the free hydroxyl group in the 3-position.

If, for example, compounds of Formula I in which Y stands for NH and wherein the substituents amino in the 3-position and $R^1$—CHR$^2$— in the 5-position are in a "cis" orientation to each other are desired, expediently a Mitsunobu reaction can be performed such that a solution of DEAD in an inert solvent named above is added to a receiving solution consisting of a solution of triphenylphosphine, a compound of Formula Ia, wherein if necessary additional hydroxyl groups present are blocked by protecting groups, and a reagent suitable for nucleophilic substitution of a hydroxyl group by an amino group in aliphatic radicals, such as phthalimide. The resulting intermediate product, for example an N-substituted phthalimide, can then be treated in a protic solvent such as a lower alkanol, for example ethanol, with a reagent suitable for releasing the resulting amine of Formula 1, such as hydrazine.

If, for example, compounds of Formula I are desired wherein Y stands for NH and wherein the substituents YH in the 3-position and $R^1$—CHR$^2$— in the 5-position are in a "trans" orientation to each other, in a compound of Formula Ia as given above first of all an inversion of the ring carbon atom in the 3-position as described above can be performed, obtaining the hydroxy substituent, and a substitution of the hydroxyl group by an amino group, as described above, with renewed inversion of the ring carbon atom in the 3-position can then be performed on this intermediate product of Formula 1.

The resulting compounds of Formula I may be isolated from the reaction mixture in known manner. Any protecting groups may if desired be cleaved off again in known manner, optionally selectively, and the group YH may if desired be blocked with known protecting groups. The possibly released NH group in the 1-position of the cyclic parent structure may if desired be reacted with the above-mentioned reagents capable of N-alkylation or of amide formation, or be blocked with an amino protecting group. If desired, compounds of Formula I which contain basic amino groups may be converted into acid addition salts in known manner. Suitable acids for this purpose are, for example, mineral acids such as hydrochloric acid or sulfuric acid, or organic acids such as sulfonic acids, for example methylsulfonic acid or p-toluenesulfonic acid, or carboxylic acids such as acetic acid, trifluoroacetic acid, tartaric acid or citric acid.

The compounds of the general formulae Ia, Ib and Ic are novel compounds, and represent valuable starting materials, for example for the production of chiral catalysts for asymmetric synthesis, for the production of biologically active alkaloids or porphyrins and for the production of pharmacologically interesting compounds.

The starting compounds of Formula II can be produced in known manner.

For example, compounds of the general formula IIa

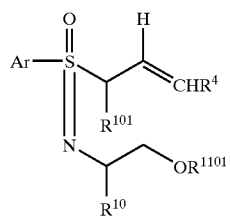

IIa wherein $R^{101}$, $R^4$, $R^{10}$, $R^{1101}$ and Ar have the above meanings, may be produced by reacting a stereoisomer of a compound of the general formula III,

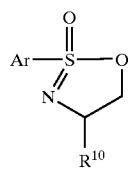

III wherein Ar and $R^{10}$ have the above meanings, with a compound of the general formula IV,

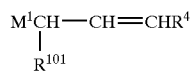

IV wherein $R^{101}$ and $R^4$ have the above meanings and $M^1$ stands for a monovalent group containing an alkali metal or an alkaline earth metal and a halogen atom, and blocking a hydroxyl group which is released if necessary upon this reaction with a silyl protecting group $R^{1101}$.

The reaction of a stereoisomer of cyclic sulfonimidates of Formula III with a metalated alkene of Formula IV to form an isomerically pure 2-alkenyl sulfoximide of Formula II can be performed in a polar or weakly polar aprotic solvent given above for the reaction of compounds of Formula II with compounds of Formula VII. Preferably, THF can be used. The reaction can be performed by mixing the reactants at a temperature of −100° C. to −50° C., preferably at −78° C., in a solvent given above and allowing the resulting reaction mixture to react for a short time, e.g. 2 to 10 minutes, at the given temperature and then warming it to a higher temperature below room temperature, for example to −20° C. to 0° C. If necessary, stirring can be continued for a while at −20° C. to 0° C. to complete the reaction. It is advantageous to use the compound of Formula IV in hyperstoichiometric quantities. For example, 1.5 to 2.5 mole of a compound of Formula IV may be reacted with one mole of a compound of Formula III.

In the cyclic sulfonimidates of Formula II, Ar may preferably stand for 4-methylphenyl (=p-tolyl). $R^{10}$ may be in particular methyl, isopropyl, isobutyl or phenyl, and preferably stands for isopropyl.

In order to achieve desired stereochemically controlled production of the compounds of Formula I, the sulfonimidates of Formula III should be used in isomerically pure form. "Isomerically pure" in the context of the present invention should be understood fundamentally to mean an excess of isomer (=excess of enantiomer, ee, or excess of diastereoisomer, de) of a pure isomer of at least 95%. In the formulae given in the context of the present invention, the "*", (asterisk) sign in each case indicates a chiral centre which is usually produced in isomerically pure manner or originates from educts usually used in isomerically pure manner. If non-isomerically pure, for example racemic, starting compounds are used to produce compounds of Formula I, of course isomer mixtures of compounds of Formula I can also be obtained using the production process according to the invention. If sulfonimidates of Formula III are used in which the chiral sulfur atom and the chiral carbon atom bearing the substituent $R^{10}$ have different absolute configurations (i.e. if, for example, the sulfur atom is in the R configuration and the carbon atom bearing the substituent $R^{10}$ is in the S configuration), particularly good results are achieved in terms of the stereochemical purity of the products of Formula I. Particularly preferably, $(R_S)$-4(R)-isopropyl-2-p-tolyl-4,5-dihydro[1.2$\lambda^6$.3]oxathiazol-2-oxide and $(S_S)$4(R)-isopropyl-2-p-tolyl-4,5-dihydro[1.2$\lambda^6$.3] oxathiazol-2-oxide may be used as compounds of Formula III. The expressions $R_S$ and $S_S$ each designate the absolute configuration at the chiral sulfur atom. Sulfonimidates of Formula III are known, for example, from Reggelin et al, Tetrahedron Letters (=TL) 33 (1992) 6959–6962 or from Reggelin et al, TL 36 (1995) 5885–5886, and may be produced in isometrically pure form according to the processes referred to therein or processes analogous thereto.

In the metalated compounds of Formula IV, the monovalent group $M^1$ may be an alkali metal, preferably lithium, or a group containing an alkaline earth metal and additionally a halogen atom. Magnesium is preferred as alkaline earth metal. Chlorine, bromine or iodine can be used as halogen. In particular, known lithiated alkenyl compounds or known magnesium-organic alkenyl compounds, such as alkenyl Grignard reagents, may be used as metalated compounds of Formula IV.

Usually, a hydroxyl group which is released upon the reaction of compounds of Formula III with compounds of Formula IV to form compounds of Formula IIa is blocked with a suitable silyl protecting group $R^{1101}$ in order to prevent undesirable subsequent reactions. Preferably trimethylsilyl (=TMS) can be used as the silyl protecting group $R^{101}$ in compounds of Formula IIa.

Compounds of the general Formula IIb,

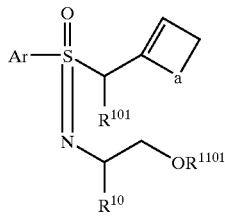

wherein $R^{101}$, $R^{10}$, $R^{1101}$ and Ar have the above meanings and a is methylene or a $C_2$–$C_5$-alkylene chain which may be bridged by $C_1$–$C_2$-alkylene which is optionally substituted one or two times by lower alkyl, may be produced, for example, by deprotonating a stereoisomer of a compound of the general formula V,

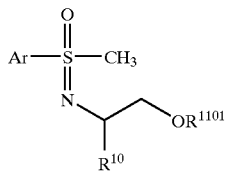

wherein $R^{10}$, $R^{1101}$ and Ar have the above meanings, with a base suitable for the deprotonation thereof, reacting the deprotonated compound of Formula V with a compound of the general formula VI,

wherein a has the above meaning, and treating the resulting intermediate product in succession with a reagent which permits cleavage of the oxygen atom derived from the carbonyl group of the compound of Formula VI and with a base given above suitable for the deprotonation of a compound of Formula V.

The reaction sequence for producing cycloalkenyl methyl sulfoximide compounds of Formula IIb by reacting compounds of Formula V with compounds of Formula VI may expediently be performed as a one-pot reaction sequence. The reaction of a stereoisomer of a methyl sulfoximide of Formula V with a base suitable for the deprotonation thereof and the following reaction steps: reaction of the deprotonated compound of Formula V with a compound of Formula VI, treatment of the resulting intermediate product with a reagent which permits the cleavage of the oxygen atom derived from the carbonyl group of the compound of Formula VI and renewed treatment with a base as stated above, are known per se and may be performed in accordance with a process mentioned in Reggelin et al, JACS 118 (1996) 4765–4777 or one analogous thereto. The group Ar and the substituent $R^{10}$ in compounds of Formula V may have the preferred meanings given above for compounds of Formula III. Preferably tert. butyl dimethylsilyl (=TBS) may be used as silyl protecting group $R^{1101}$ in compounds of Formula V. Analogously to the preferred stereochemical conditions given above for compounds of Formula III, preferably $[S_S,N(1S)]$-N-[1-[[tert. butyldimethylsilyl)oxy]methyl]-2-methylpropyl]-S-methyl-S-(4-methylphenyl) sulfoximide and $[R_S,N(1R)]$-N-[1-[[tert. butyldimethylsilyl)oxy]methyl]-2-methylpropyl]-S-methyl-S-(4-methylphenyl) sulfoximide may be used as compounds of Formula V. Lithiated lower alkyl compounds such as n-butyllithium are, for example, suitable as bases for deprotonation of compounds of Formula V. The compounds named above for the formation of a good leaving group by attack on the oxygen atom of the sulfonyl group in compounds of Formula Xa are suitable as reagents which permit the cleavage of oxygen atoms derived from the carbonyl group of compounds of Formula VI. Preferably, TMS triflate can be used.

The alicyclic ketones of Formula VI are known. For example, cyclopentanone, cyclohexanone or nopinone may be used as compounds of Formula VI. If bridged cyclic ketones are used as compounds of Formula VI, it is advantageous if the bridging alkylene chain is bonded to at least one of the two carbon atoms in the α-position to the carbonyl group. In this manner, the reaction products are always formed with controlled regioselectivity.

Another possible way of obtaining compounds of Formula IIb is the reaction of a compound of the general formula XII,

wherein a and Ph have the above meanings, each with a reagent suitable for the lithiating deselenation thereof and the subsequent reaction of the deselenated lithiated intermediate product produced in each case with a stereoisomer of a compound of Formula III.

The selenated compounds of Formula XII can be obtained in known manner from the corresponding allyl alcohols by halogenation and subsequent reducing selenation. For example, the compounds of Formulae XII may be obtained according to the process mentioned by Reggelin et al in JACS 118 (1996) 4765–4777 or to processes analogous thereto. Myrtenol may be mentioned as an example of an allyl alcohol which is suitable for the production of selenated compounds of Formula XII.

The production of compounds of Formula IIb by reaction of compounds of Formula XII with compounds of Formula III can be performed in known manner, for example in accordance with the method for the production of cycloalkenyl sulfoximide compounds referred to in the publication by Reggelin et al, JACS 118 (1996) 4765–4777, to which reference is expressly made hereby.

In one variant of the invention, compounds of Formula II wherein $R^{101}$ has a meaning other than hydrogen can be produced by simply deprotonating compounds of Formula II wherein $R^{101}$ stands for hydrogen with a base suitable for this purpose, and then alkylating them by reaction with a compound of the general formula XI, $$R^{103}\text{—}Z \qquad\qquad XI$$

wherein $R^{103}$ has the meaning given for $R^{101}$ with the exception of hydrogen and Z stands for a cleavable leaving group. Suitable examples of bases for a deprotonation as referred to above are, for example, lithiated lower alkyl compounds such as n-butyllithium. Halogen, preferably bromine or chlorine, may for example be used as cleavable leaving group Z in compounds of Formula XI. The reaction can be performed under conventional reaction conditions for this type of reaction.

The following examples are intended to explain the invention further, without restricting its scope.

The numbering of the ring atoms in the example compounds, in particular of the chiral carbon atoms, relates to the numbering of the ring atoms given in general formula 1.

EXAMPLE 1

(+)-(2S,3S,4S,5S)-2-isobutyl-3-hydroxy-4,5-dimethyl-N-tert. butoxycarbonyl-pyrrolidine A) 6.0 g FMOC-amino-protected S-2-amino-4-methylpentanol (obtained by lithium aluminium hydride reduction of leucine) was suspended in 100 ml dichloromethane under a nitrogen atmosphere and with water excluded and cooled to 0° C. To this receiving solution was added 10.0 g 1,1,1-triacetoxy-1,1-dihydro-1,2-benziodoxol-3(1H)-one (=periodinane) in one portion as a solid, and the resulting reaction mixture was stirred for two hours at room temperature. Then the reaction mixture was poured onto a solution of 130 ml of a 10% strength aqueous sodium thiosulfate solution and 360 ml of a saturated aqueous sodium hydrogen carbonate solution covered with 100 ml ether. The aqueous phase was extracted once with 100 ml ether, the combined organic phases were washed with a saturated aqueous sodium chloride solution and were dried over sodium sulfate. The solvent was evaporated under reduced pressure and the crude FMOC-protected S-2-amino-4-methyl valeraldehyde obtained in this manner was used for the following reaction without further purification.

To determine the optical purity, a portion of the resulting aldehyde was isolated by crystallisation from ether/hexane. The excess of enantiomer was determined by NMR spectroscopy with addition of the chiral shift reagent tris-[3-(heptafluoropropyl-hydroxymethylene)-d-camphorato]-praseodymium (III) [=Pr(hfc)$_3$]. The excess of enantiomer (ee) was determined as 95% by integration of the baseline-separated signals of the aldehyde protons.

B) 1.82 g magnesium chippings were covered with approximately 10 ml diethyl ether and activated by addition of 500 mg freshly distilled crotyl bromide. A solution of 10.0 g crotyl bromide (=cis/trans-1-bromo-2-butene) in 100 ml diethyl ether was added slowly dropwise to this receiving solution at 0° C. with protection by argon and with moisture excluded. The resulting mixture was heated to boiling for 30 minutes once addition had taken place. The resulting ethereal solution of crotyl magnesium bromide was separated from non-reacted magnesium and was reacted further directly in solution without further working-up.

To determine the content of the Grignard solution produced above, a solution of 180 mg (−)-menthol and a spatula-tip of phenanthroline in 3.0 ml THF was cooled to 0° C. By adding the Grignard solution to this receiving solution, titration was performed until the colour changed to red, and the quantity of Grignard solution required for the following reaction was determined by differential weighing. The content of the Grignard solution in mmol/g is yielded from the quotient of the quantity of menthol weighed in in mmol and the weight in g of the Grignard solution required for titration until the colour change.

C) 46 g of the solution of crotyl magnesium bromide dissolved in 100 ml diethyl ether obtained above was added dropwise to a solution of 2.3 g (+)—(R$_S$)-4(R)-isopropyl-2-p-tolyl-4,5-dihydro[1.2$\lambda^6$.3]oxathiazol-2-oxide in 40 ml THF cooled to −40° C., with protection by argon and with moisture excluded. Once addition had been completed, stirring was carried out for five minutes at the given temperature before the reaction mixture was allowed to warm to 0° C. Stirring was continued at this temperature for a further 45 minutes, and then 50 ml of a saturated aqueous ammonium chloride solution was added. The organic phase was separated, the aqueous phase was extracted twice with ether and the combined organic phases were dried over sodium sulfate. Then the solvent was evaporated under reduced pressure and the residue was chromatographed over silica gel (mobile solvent: initially ethyl acetate/n-hexane 1:3 v/v, the composition of which was continuously changed up to 3:1). 1.4 g (R$_S$,1R)-N-[1-(hydroxymethyl)-2-methyl-propyl]-S-(2-butenyl)-p-toluenesulfoximide was obtained as a colourless oil, IR (film)=3440, 1220, 1115 cm$^{-1}$, optical rotation [α]$_D^{20}$=+3.3° (c=0.5 in dichloromethane).

D) 0.6 ml chlorotrimethylsilane was added dropwise to a solution of 1.4 g of the sulfoximide obtained above and 0.7 ml ethyl dimethylamine in 13 ml dichloromethane which had been cooled to 0° C., with protection by argon and with moisture excluded. Once addition had been completed, stirring was continued for 15 minutes at 0° C. Then the solution was allowed to thaw to room temperature and once complete reaction had taken place the reaction mixture was poured onto a mixture of 25 ml ether and 25 g ice. The aqueous phase was extracted three times with 10 ml ether each time, the organic phases were combined and dried over magnesium sulfate. The solvent was evaporated under reduced pressure, and the remaining residue was purified by chromatography on silica gel (mobile solvent: ether/n-hexane 1:1 v/v). 1.75 g (+)(R$_S$,1R)-N-[1-(trimethylsilyloxy-methylpropyl)-2-methyl]-S-(2-butenyl)-p-toluenesulfoximide was obtained as a colourless oil, IR (film)=1240, 1080, 840 cm$^{-1}$, optical rotation [α]$_D^{20}$ =+15.5° (c=1.0 in dichloromethane).

E) A solution of 1.47 g of the TMS-protected 2-alkenyl sulfoximide obtained above in 8 ml toluene was cooled to −78° C. and 2.75 ml of a 1.6-molar solution of n-butyllithium in n-hexane was added thereto with protection by argon and with moisture excluded. The reaction mixture was stirred for 15 minutes at the temperature given, and then 4.8 ml of a 1-molar solution of chlorotris(isopropoxy)titanium in n-hexane was added thereto. Stirring was continued for another 5 minutes at −78° C., the mixture was thawed to 0° C. and then stirred for another 30 minutes at 0° C. Then the reaction mixture was cooled again to −78° C. A solution of 2.8 g of the aminoaldehyde obtained above under A) in 8 ml THF was added to this receiving solution. Stirring was continued for 60 minutes at −78° C., 4 ml piperidine was added and the mixture was warmed to 0° C. After 10 hours, the reaction mixture was poured onto 120 ml of a thoroughly stirred, saturated ammonium carbonate solution covered with 12 ml ethyl acetate (=EA). This mixture was stirred for 30 minutes and then the phases were separated. The organic phase was washed with 40 ml of a saturated ammonium chloride solution and the combined aqueous phases were extracted three times with EA. The combined organic phases were dried over sodium sulfate and the solvent was evaporated under reduced pressure. The remaining residue was taken up with a suspension of 0.6 g potassium carbonate in 10 ml methanol and was stirred for 60 minutes. Then non-dissolved potassium carbonate was filtered out and the filtrate was cooled to 4° C. Precipitated solid was filtered out, washing was effected with a little methanol which was at a temperature of 4° C. and the filtrate was evaporated under reduced pressure. The resulting residue was taken up in 5 ml toluene and filtered over silica gel (mobile solvent: initially ether/hexane 1:3 v/v then EA). The polar, pyrrolidine-containing fraction was reduced and taken up in 4 ml dioxan. 1.0 g di-tert. butyldicarbonate [=(BOC)$_2$O] and a solution of 0.7 g sodium hydrogen carbonate in 8 ml water were added to this receiving solution. The mixture was stirred for 10 hours, the solvent was evaporated under reduced pressure and the remaining residue was distributed between 5 ml water and 10 ml ether. The aqueous phase was extracted three times with ether and the combined organic phases were dried over sodium sulfate. After renewed evaporation of the solvent under reduced pressure, the resulting residue was purified by chromatography on silica gel (mobile solvent: ether/hexane 3:1 v/v). 1.0 g (R$_S$,1'R,2S,3S,4S,5R)-N'-[(1-hydroxymethyl)-2-(methylpropyl)]-S-4-hydroxy-3-methyl-2-(4-methylphenylsulfonimidoylmethyl)-5-isobutyl-N-tert. butoxycarbonyl-pyrrolidine was obtained as a colourless foam, optical rotation $[\alpha]_D^{20}=-4°$ (c=0.1 in dichloromethane), IR (film)=3419, 1674, 1256, 1097 cm$^{-1}$.

F) A total of 2.4 g diiodomethane was added dropwise to a suspension of 1.67 g samarium in 40 ml THF which had been cooled to 0° C. Once addition had taken place, the mixture was stirred for 15 minutes at 0° C. before the reaction mixture was thawed to room temperature. Stirring was continued for another 60 minutes at room temperature, and then a solution of 1.0 g of the 2-sulfonimidoylmethyl compound obtained above in a mixture of 1.2 ml methanol and 2.5 ml THF was added. The reaction mixture was stirred for 4 hours and then 110 ml saturated aqueous ammonium chloride solution was added thereto. After the first phase separation, 0.5 N aqueous hydrochloric acid solution was added dropwise to the aqueous phase until the phase cleared. The aqueous phase was extracted three times with ether. The combined organic phases were dried over sodium sulfate and the solvent was evaporated under reduced pressure. Chromatography of the remaining residue on silica gel (mobile solvent: ether/n-hexane 3:1 v/v) yielded 0.5 g of the title compound as a colourless solid, melting point 97° C., optical rotation $[\alpha]_D^{20}=+66°$ (c=1.0 in dichloromethane).

EXAMPLE 2

(+)-(2S,3S,4S,5R)-3-hydroxy-5-methyl-2-phenyl-(1-aza-N-tert. butoxycarbonyl)-bicyclo[3.3.0]octane A) 16.6 ml of a 1,6-molar solution of methyllithium in hexane was added dropwise to a solution of 3.98 g (+)-(R$_S$)-4R-isopropyl-2-p-tolyl-4,5-dihydro[1.2λ$^6$.3] oxathiazol-2-oxide in 40 ml THF cooled to −78° C., with protection by argon and with moisture excluded. Once addition had been completed, stirring was continued for five minutes at the given temperature before the reaction mixture was allowed to warm to 0° C. Stirring was continued at this temperature for a further 45 minutes, and then 160 ml ammonium chloride was added. Once the organic phase had been separated, the aqueous phase was extracted twice with 20 ml ether and the combined organic phases were dried over sodium sulfate. Then the solvent was evaporated under reduced pressure. The remaining residue was dissolved in 80 ml dichloromethane at room temperature, and 3.8 g tert. butyldimethylsilyl chloride, 0.6 g N,N-dimethylaminopyridine and 2.4 g ethyldimethylamine were added thereto and the mixture was stirred for 18 hours. Then the mixture was poured on to 40 ml ice water, the organic phase was separated and the aqueous phase was extracted three times with 20 ml dichloromethane each time. After drying the combined organic phases over sodium sulfate, the solvent was evaporated under reduced pressure. Purification of the residue over silica gel (mobile solvent: ether/n-hexane 1:1 v/v) yielded 6.0 g (−)-R$_S$-N(1R)-N-[1-((tert. butyidimethylsilyl)oxy)-methyl-2-methylpropyl]-S-methyl-S-(4-methylphenyl)sulfoximide as a colourless oil, optical rotation $[\alpha]D_D^{20}=43.2°$ (c=0.8 in dichloromethane); IR (film)=1230, 1130 cm$^{-1}$.

B) 12.45 ml of a 1.6-molar solution of n-butyllithium in n-hexane was added dropwise to a solution of 6.5 g of the methylsulfoximide obtained above in 45 ml toluene, which solution had been cooled to −78° C., with protection by argon and with moisture excluded. Stirring was carried out for 15 minutes at the temperature given and then 2.2 g cyclopentanone was added undiluted thereto in drops. After 10 minutes, the reaction mixture was warmed to room temperature. Stirring was continued for a further 30 minutes at this temperature before the batch was cooled to −78° C. and 9.2 g trimethylsilyltrifluoro-methyl sulfonate was added thereto in drops. After five minutes, the mixture was warmed to room temperature and was stirred for a further three hours. Once it had been cooled again to −78° C., 24.9 ml of a 1.6-molar solution of n-butyllithium in n-hexane was added dropwise thereto. After three minutes' stirring at the given temperature, the mixture was allowed to thaw to room temperature and stirring was continued for another 18 hours. The reaction mixture was poured on to 160 ml of a saturated aqueous ammonium chloride solution, the mixture was extracted twice with ethyl acetate and the combined organic phases were dried over sodium sulfate. The solvent was evaporated under reduced pressure and the remaining residue was purified over silica gel (mobile solvent: ether/n-hexane 1:6 v/v). 5.5 g (−)-R$_S$-N(1R)-N-[1-((tert. butyldimethylsilyl)oxy)methyl-2-methylpropyl]-S-cyclopent-1-en-1-ylmethyl)-S-(4-methylphenyl) sulfoximide was obtained as a colourless oil, optical rotation $[\alpha]_D^{20}=-2.5°$ (c=1.6 in dichloromethane), IR (film)=1240, 1120 cm$^{-1}$.

C) In the manner described above under 1E), a solution of 2.95 g of the cyclopentenyl sulfoximide obtained above in 21 ml toluene was reacted with 4.8 ml of a 1.6-molar solution of n-butyllithium in n-hexane, 8.3 ml of a 1-molar solution of chlorotris(isopropoxy)titanium in n-hexane, a solution of 5.0 g FMOC-protected S-α-aminophenylethanal in 40 ml THF and 7 ml piperidine. Chromatography on silica gel (mobile solvent: ether/n-hexane=1:3 v/v) yielded 3.9 g (2S,3S,4S,5R)R$_S$-N(1 R)-N-[1-((tert. butyidimethylsilyl)oxy)methyl-2-methylpropyl]-3-hydroxy-2-phenyl-5-(4-methylphenyl) sulfonimidoylmethyl-2-azabicyclo[3.3.0]octane. Optical rotation $[\alpha]_D^{20}+2.8°$ (c=0.6 in dichloromethane); IR (film)=3443, 1251, 1103, 835 cm$^{-1}$.

D) 0.45 g sodium hydrogen carbonate and 3.0 g di-tert. butyl dicarbonate were added to a solution of 3.9 g of the bicyclic compound obtained above in 20 ml dichloromethane and 40 ml water, and the mixture was stirred for 12 hours. Once the solvent had been evaporated under reduced pressure, the resulting residue was distributed between 5 ml water and 10 ml ether. The organic phase was separated, and the aqueous phase was extracted twice with ether. Drying of the combined organic phases over sodium sulfate, evaporation of the solvent under reduced pressure and chromatography of the remaining residue on silica gel (mobile solvent: ether/n-hexane=1:1 v/v) yielded 4.39 g (−)-(2S,3S,4S,5S)-(-R$_S$-N(1R)N-[1-((tert. butyldimethylsilyl)oxy)methyl-2-methylpropyl]-3- hydroxy-2-phenyl-5-(4-methylphenylsulfonimidoyl-methyl-2-aza-(N-tert. butoxycarbonyl)-bicyclo[3.3.0]octane, optical rotation $[\alpha]_D^{20}=-6.2°$ (c=0.9 in dichloromethane); IR (film)=3473, 1682, 1253, 837 cm$^{-1}$.

E) 0.25 g tetrabutylammonium fluoride was added to a solution of 0.42 g of the bicyclic compound protected at the nitrogen obtained above in 6 ml THF, which solution had been cooled to 0° C., the mixture was warmed to room temperature after 15 minutes and then stirred for another 12 hours. The reaction mixture was poured on to 10 ml water which was covered with 5 ml ether. Once the organic phase had been separated, the aqueous phase was extracted three times with ether, the combined organic phases were dried over sodium sulfate and the solvent was evaporated under reduced pressure. Chromatography on silica gel (mobile solvent: ethyl acetate/n-hexane=1:1 v/v) yielded 0.35 g (−)-(2S,3S,4S,5S)-R$_S$-N(1R)-N-[1-(hydroxymethyl)-2-methylpropyl]-3-hydroxy-2-phenyl-5-(4-methylphenylsulfonimidoylmethyl-2-aza-(N-tert. butoxycarbonyl)-bicyclo[3.3.0]octane. $[\alpha]_D^{20}=-14.1$ (c=2.7 in dichloromethane); IR (film)=3473, 1681, 1252 cm$^{-1}$.

F) A total of 0.84 g diiodomethane was added dropwise to a suspension of 0.56 g samarium in 13 ml THF which had been cooled to 0° C. Once addition had taken place, the mixture was stirred for 15 minutes at the given temperature before the reaction mixture was thawed to room temperature. Stirring was continued for another 60 minutes, and then a solution of 0.28 g of the N-BOC-5-sulfonimidoyl compound obtained above in a mixture of 1 ml methanol and 2 ml THF was added. The reaction mixture was stirred for four hours and then poured on to 110 ml of a saturated ammonium chloride solution. Once the organic phase had been separated, 0.5 N hydrochloric acid solution was added to the aqueous phase until the suspension had cleared. The clear aqueous phase was extracted twice with ether, the combined organic phases were dried over sodium sulfate and the solvent was evaporated under reduced pressure. Chromatography of the remaining residue on silica gel (mobile solvent: ether/n-hexane=1:4 v/v) yielded 0.11 g of the title compound as a colourless solid body, melting point 176.8° C., $[\alpha]_D°=+50.7°$ (c=0.56 in dichloromethane); IR (film)=3439, 1661 cm$^{-1}$.

EXAMPLE 3

(+)-(2S,3R,4R,5S)-3-hydroxy-5-methyl-2-phenyl-1-aza-(N-tert. butoxycarbonyl)-bicyclo[3.3.0]octane A) 6.3 g (−)-S$_S$-4R-isopropyl-2-p-tolyl-4,5-dihydro[1.2λ$^6$.3]oxathiazol-2-oxide was reacted with 6.03 g tert. butyldimethylsilyl chloride corresponding to the manner described in Example 2A). 8.7 g (+)-S$_S$-N(1R)-N-[1-((tert. butyidimethylsilyl)oxy)-methyl-2-methylpropyl]-S-methyl-S-(4-methyl-phenyl)sulfoximide was obtained as a colourless oil, optical rotation $[\alpha]_D^{20}=+89.9°$ (c=1.0 in dichloromethane), IR (film): 1251, 1134 cm$^{-1}$.

B) In the manner described above under 2B), a solution of 8.04 g of the methyl sulfoximide obtained above in 65 ml THF was reacted with 16.3 ml of a 1.6-molar solution of n-butyllithium in n-hexane, 3.1 ml cyclopentanone, 9.83 ml trimethylsilyltrifluoromethane sulfonate and a further 27.19 ml of a 1.6-molar solution of n-butyllithium in n-hexane. Chromatography on silica gel (mobile solvent: ether/n-hexane=1:6 v/v) yielded 7.057 g (+)S$_S$-N((1R)-N-[1-((tert. butyidimethylsilyl)oxy)methyl-2-methylpropyl]-S-cyclopent-1-en-1-ylmethyl)-S-(4-methylphenyl)-sulfoximide as a colourless oil, optical rotation $[\alpha]_D^{20}=+54.7°$ (c=1.35 in dichloromethane), IR=1251, 1131 cm$^{1}$.

C) In the manner described above under 1E), a solution of 3.17 g of the cyclopentenyl sulfoximide obtained above in 22 ml toluene was reacted with 5.6 ml of a 1.6 molar solution of n-butyllithium in n-hexane, 11.2 ml of a 1-molar solution of chlorotris(isopropoxy)titanium in n-hexane, a solution of 4.0 g FMOC-protected S-α-aminophenylethanol in 20 ml THF and 7.4 ml piperidine. Chromatography on silica gel (mobile solvent: ether/n-hexane=1:1 v/v) yielded 2.4 g (2S,3R,4R,5S)-S$_S$-N(1R)-N-[1-((tert. butyldimethylsilyl)oxy)methyl-2-methylpropyl]-3-hydroxy-2-phenyl-5-(4-methylphenyl)sulfonimidoylmethyl-2-azabicyclo[3.3.0]octane.

D) 0.35 g sodium hydrogen carbonate and 1.21 g di-tert. butyl dicarbonate were added to a solution of 1.58 g of the bicyclic compound obtained above in 17 ml dioxan and 4 ml water, and the mixture was stirred for 12 hours. Once the solvent had evaporated under reduced pressure, the resulting residue was distributed between 5 ml water and 10 ml ether. The organic phase was separated and the aqueous phase was extracted twice with ether. Drying of the combined organic phases over sodium sulfate, evaporation of the solvent under reduced pressure and chromatography of the remaining residue on silica gel (mobile solvent: ether/n-hexane 1:1 v/v) yielded 1.52 g (+)-(2S,3R,4R,5S)-S$_S$-N(1R)-N-[1-((tert. butyidimethylsilyl)oxy)methyl-2-methylpropyl]-3-hydroxy-2-phenyl-5-(4-methylphenylsulfonimidoylmethyl-(2-aza-N-tert. butoxycarbonyl)-bicyclo[3.3.0]octane, optical rotation $[\alpha]_D^{20}=+63.2°$ (c=1.0 in dichloromethane); IR (film)= 3473, 1694, 1254, 836 cm$^{-1}$.

E) 1.43 g tetrabutylammonium fluoride was added to a solution of 1.52 g of the bicyclic compound protected at the nitrogen obtained above in 14 ml THF, which solution had been cooled to 0° C., the mixture was warmed to room temperature after 15 minutes and then stirred for another 12 hours. The reaction mixture was poured on to 30 ml water which was covered with 20 ml ether. Once the organic phase had been separated, the aqueous phase was extracted three times with ether, the organic phase was dried over sodium sulfate and the solvent was evaporated under reduced pressure. Chromatography on silica gel (mobile solvent: ethyl acetate/n-hexane=1:3 v/v) yielded 0.96 g (+)-(2S,3R,4R,5S)-S$_S$-N(1R)-N-[1-hydroxymethyl-2-methylpropyl]-3-hydroxy-2-phenyl-5-(4-methylphenylsulfonimidoylmethyl-(2-aza-N-tert. butoxycarbonyl)-bicyclo[3.3.0]octane, optical rotation $[\alpha]_D^{20}=+54.3°$ (c=1.03 in dichloromethane); IR (film)= 3446, 1690, 1239 cm$^{-1}$.

F) 3.4 g diiodomethane was added to a suspension of 2.04 g samarium in 95 ml THF at room temperature, and the mixture was stirred for 60 minutes. Then a solution of 0.955 g of the 5-sulfonimidoyl compound obtained above in a mixture of 1.7 ml methanol and 3.4 ml THF was added. The reaction mixture was stirred for 16 hours and then poured on to 100 ml water. 0.5 N hydrochloric acid solution was added to the mixture until the suspension had cleared. The phases were separated and the aqueous phase was extracted twice with ether, the combined organic phases were dried over sodium sulfate and the solvent was evaporated under reduced pressure. Chromatography of the remaining residue on silica gel (mobile solvent: ether/n-hexane=1:3 v/v) yielded 0.43 g of the title compound as a colourless, solidifying oil (foam), optical rotation $[\alpha]_D^{20}=+34.5°$ (c=1.01 in dichloromethane); IR (film)= 3447, 1669 cm$^{-1}$.

EXAMPLE 4

(−)-(2S,3R,4R,5S)-3-hydroxy-5-methyl-2-phenyl-1-azabicyclo[3.3.0]octane 205 mg (+)-(2S,3R,4R,5S)-3-hydroxy-5-methyl-2-phenyl-1-aza-(N-tert. butoxycarbonyl)-bicyclo[3.3.0]octane (for preparation see Example 3) was dissolved, under argon atmosphere and with moisture excluded, in a mixture consisting of 1.61 ml of a 4.0 M chlorotrimethylsilane solution in dichloromethane and 4.84 ml of a 4.0 M phenol solution in dichloromethane, and the mixture was stirred for 20 minutes at room temperature. Then it was poured on to 10 ml of a 10% strength aqueous sodium hydroxide solution, the organic phase was separated, the aqueous phase was extracted twice with 5 ml dichloromethane each time and once with 5 ml ether, and the combined organic phases were dried over magnesium sulfate. The solvent was evaporated under reduced pressure, and the residue was purified over silica gel (mobile solvent: ethyl acetate/n-hexane 10:1 v/v). 113 mg crystalline title compound was obtained, melting point=84.5° C., optical rotation $[\alpha]_D^{20}$=−46.4° (c=1.04 in dichloromethane).

EXAMPLE 5

(+)-(2S,3S,4R,5S)-3-amino-5-methyl-2-phenyl-1-aza-(N-tert. butoxycarbonyl)-bicyclo[3.3.0]octane A) 241 mg triphenylphosphine and 135 mg phthalimide were added to a solution of 200 mg (−)(2S,3R,4R,5S)-3-hydroxy-5-methyl-2-phenyl-1-azabicyclo[3.3.0]octane in 1.5 ml THF at room temperature under an argon atmosphere and with moisture excluded. Then 0.14 ml DEAD was added within 2 minutes. After a reaction time of 10 hours, the solvent was evaporated under reduced pressure and the residue was taken up in 5 ml ether. Once undissolved residue had been filtered out and the solvent evaporated under reduced pressure, (2S,3S,4R,5S)-5-methyl-2-phenyl-3-phthalimido-1-azabicyclo[3.3.0]octane was obtained as crude product, which was used for the subsequent reaction without further purification.

B) 174 mg of the crude product obtained above was dissolved in 3 ml dioxan. 220 mg di-tert. butyl dicarbonate and 63 mg sodium hydrogen carbonate and also 0.5 ml water were added to this receiving solution and the resulting mixture was stirred for 16 hours at room temperature. The solvent was evaporated under reduced pressure and the remaining residue was taken up in water and ether. The phases were separated and the aqueous phase was extracted twice with 5 ml ether each time. The combined organic phases were dried over magnesium sulfate before the solvent was evaporated under reduced pressure. Chromatography of the remaining residue on silica gel (mobile solvent: ether/n-hexane 1:3 v/v) yielded 115 mg oily (2S,3S,4R,5S)-5-methyl-2-phenyl-3-phthalimido-1-aza-(N-tert. butoxycarbonyl)-bicyclo[3.3.0]-octane.

C) 400 mg hydrazine hydrate (24% strength) was added to a solution of 115 mg of the phthalimido-bicyclo[3.3.0]octane obtained above in 2 ml ethanol and the resulting mixture was heated to reflux for 8 hours. The solvent was evaporated under reduced pressure, the remaining residue was taken up in 10 ml ether and the organic phase was extracted with 10 ml of a 10% strength aqueous sodium hydroxide solution. The aqueous phase was extracted twice with 10 ml ether in each case, and the combined organic phases were dried over magnesium sulfate. The solvent was evaporated under reduced pressure, and 74 mg crystalline title compound was obtained, melting point=92.1° C., $[\alpha]_D^{20}$=+24.1° (c =1.0 in dichloromethane).

The compounds of Formula I listed in the table below can also be produced according to the methods given above.

The following abbreviations are used in the table:

| | | | | | | | | | | Absolute config. at C-atom No. | | | | | | | |
|---|---|---|---|---|---|---|---|---|---|---|---|---|---|---|---|---|---|
| Ex. No. | R¹ | R² | R³ | R⁴ | R⁵ | R⁶ | R⁷ | R⁸ | R⁹ | 2 | 2a | 3 | 4 | 6 | Y | n | Mp [° C.] | $[\alpha]_{20}^D$ |
| 6 | N.N. | | | | | | | | | | | | | | | | | |
| 7 | H | H | H | H | — | — | H | Bn | BOC | S | — | R | — | R | O | 0 | 108.5 | −37.7 |
| 8 | H | H | H | H | — | — | H | i-Bu | BOC | S | — | R | — | R | O | 0 | Oil | +28.2 |
| 9 | H | H | H | H | — | — | H | TBOM | BOC | S | — | R | — | R | O | 0 | 115.7 | +24.5 |
| 10 | H | H | H | CH₃ | — | — | H | Bn | BOC | S | — | R | R | R | O | 0 | 127.8 | −37.3 |
| 11 | H | H | H | CH₃ | — | — | H | TBOM | BOC | S | — | R | R | R | O | 0 | Oil | +14.8 |
| 12 | H | H | H | H | — | — | H | Bn | BOC | S | — | S | — | S | O | 0 | 107.7 | +6.5 |
| 13 | H | H | H | H | — | — | H | i-Bu | BOC | S | — | S | — | S | O | 0 | Oil | −37.3 |
| 14 | H | H | H | H | — | — | H | TBOM | BOC | S | — | S | — | S | O | 0 | 93.1 | +1.8 |
| 15 | H | H | H | CH₃ | — | — | H | Bn | BOC | S | — | S | S | S | O | 0 | 91.0 | +26.7 |
| 16 | H | H | H | CH₃ | — | — | H | i-Bu | BOC | S | — | R | R | R | O | 0 | 97.0 | −20.0 |
| 17 | H | H | H | CH₃ | — | — | H | TBOM | BOC | S | — | S | R | S | O | 0 | 187.2 | −20.8 |
| 18 | H | H | —(CH₂)₃— | — | — | H | Bn | BOC | S | — | R | R | S | O | 0 | 136.7 | +8.2 |
| 19 | H | H | —(CH₂)₃— | — | — | H | Bn | H | S | — | R | R | S | O | 0 | 117.2 | −60.7 |
| 20 | H | H | —(CH₂)₃— | H | H | H | H | H | — | — | S | R | S | O | 1 | | |
| 21 | H | H | —(CH₂)₄— | H | H | H | H | H | — | — | S | R | S | O | 1 | | |
| 22 | H | H | —(CH₂)₃— | =CH—CH=CH—CH= | H | — | — | R | R | S | O | 1 | | | | | | |
| 23 | H | H | —(CH₂)₃— | — | — | H | Bn | BOC | S | — | S | S | S | NH | 0 | 94.6 | +48.9 |
| 24 | H | H | —(CH₂)₃— | — | — | H | Bn | H | S | — | S | S | S | NH | 0 | HCl-Salt (Z.) | |
| 25 | H | H | —(CH₂)₃— | H | H | H | H | BOC | — | — | S | R | S | O | 1 | Oil | −17.7 |
| 26 | H | H | —(CH₂)₄— | H | H | H | H | BOC | — | — | S | R | S | O | 1 | Oil | −19.8 | i-Bu = isobutyl
Bn = benzyl
BOC = tert. butoxycarbonyl
TBOM = tert. butoxymethyl
Ph = phenyl
Z. = decomposition upon heating
N.N. = entry not noted

What is claimed is:

1. A process for stereochemically controlled production of a compound corresponding to formula I:

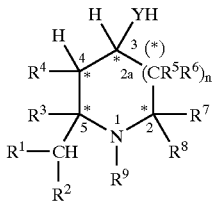

wherein the $R^1R^2CH$ group in the 5-position of the cyclic parent structure and the hydroxy group in the 3-position of the cyclic parent structure are each in the trans position relative to each other and wherein the substituent $R^4$ in the 4-position and the hydroxy group in the 3-position of the cyclic parent structure are each in the cis position relative to each other, and wherein n is 0 or 1,
$R^1$ is hydrogen;
$R^2$ is hydrogen;
$R^3$ is hydrogen, and
$R^4$ is hydrogen or lower alkyl, or
$R^3$ and $R^4$ also together are a $C_3$–$C_6$-alkylene chain optionally containing 1 to 3 double bonds or together form the 7,7-dimethylbicyclo[3.1.1]heptyl-system
$R^5$ is hydrogen or lower alkyl, and
$R^6$ is hydrogen, and
$R^7$ is hydrogen, and
$R^8$ is hydrogen;
    a monocyclic or bicyclic ring system selected from the group consisting of cyclopropyl, cyclopentyl cyclohexyl, phenyl, p-bromophenyl and 3-indolyl; lower alkyl; phenyl-lower alkyl or lower-alkoxy lower alkyl, or
$R^6$ and $R^7$ also together may form a bond, and
$R^5$ and $R^8$, together with the carbon atoms to which they are bonded, may form an aromatic $C_6$-ring system,
$R^9$ is hydrogen; lower alkyl; phenyl-lower alkyl optionally substituted one to three times in the phenyl ring by lower alkyl, lower haloalkyl, lower alkoxy or lower haloalkoxy; or an amino protecting group, or
$R^8$ and $R^9$ also together may form a $C_3$–$C_4$-alkylene chain, and
Y is oxygen
or an acid addition salt thereof, wherein any reactive groups which may be present in said compound of Formula I may be blocked by suitable protecting groups,
said process comprising the steps of:
a) reacting a compound corresponding to formula II:

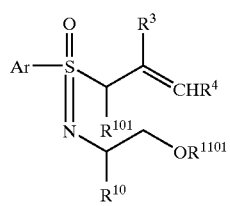

wherein
$R^3$ and $R^4$ have the above meanings,
$R^{101}$ has the meaning given above for $R^1$ Ar represents phenyl optionally substituted one to three times by lower alkyl,
$R^{10}$ is lower alkyl, or phenyl optionally substituted once in the phenyl ring by lower alkyl or by hydroxy protected with a suitable protecting group, or phenyl-lower alkyl optionally substituted once in the phenyl ring by lower alkyl, and
$R^{1101}$ stands for a silyl protecting group,
successively with
    (i) a base for the deprotonation thereof,
    (ii) an organometallic reagent corresponding to the formula VII:

$$XM^2(OR^{12})_3 \qquad \text{VII}$$

wherein
X is halogen,
$M^2$ is a tetravalent transition metal, and
$R^{12}$ is lower alkyl, phenyl or phenyl-lower alkyl, and
    (iii) a stereoisomer of a compound of the general formula VIII:

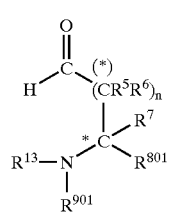

wherein
$R^5$, $R^6$, $R^7$ and n have the above meanings,
$R^{801}$ has the meaning of $R^8$, with any reactive groups, if necessary, being blocked by base-stable protecting groups,
$R^{901}$ is hydrogen or together with $R^{801}$ forms a $C_3$–$C_4$-alkylene chain, and
$R^{13}$ is a base-labile amino protecting group which when cleaved leaves behind a nitrogen nucleophile,
to form a stereoisomer of a compound corresponding to the formula IX:

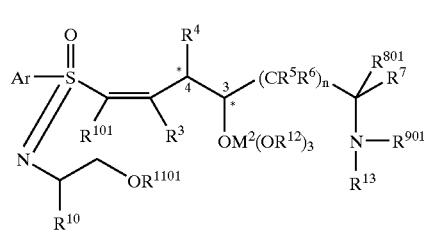

wherein
$R^{101}$, $R^3$, $R^4$, $R^5$, $R^6$, $R^7$, $R^{801}$, $R^{901}$, $R^{10}$, $R^{1101}$, $R^{12}$, $R^{13}$, n, Ar and M2 have the above meanings, and
b) converting the compound of Formula IX by treatment with a base reagent for removing the group $R^{13}$, into a compound corresponding to formula Xa:

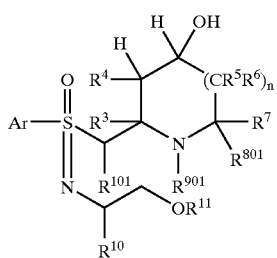

wherein
$R^{101}$, $R^3$, $R^4$, $R^5$, $R^6$, $R^7$, $R^{801}$, $R^{901}$, $R^{10}$, n and Ar have the above meanings, and $R^{11}$ is hydrogen or a silyl protecting group, and if $R^{901}$ is hydrogen, blocking the nitrogen atom in the cyclic parent structure of the resulting compound of Formula Xa with a base-stable protecting group, and cleaving off any silyl protecting group $R^{11}$ which may still be present; and c) for the production of a compound corresponding to formula Ia:

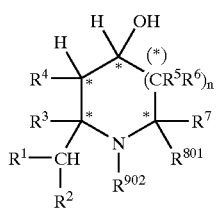

wherein
$R^1$, $R^2$, $R^3$, $R^4$, $R^5$, $R^6$, $R^7$, $R^{801}$ and n have the above meanings, and $R^{902}$ stands for a base-stable protecting group or, together with $R^{801}$, for a $C_3$–$C_4$-alkylene chain, reacting a compound corresponding to formula Xa or a compound produced by cleaving off the silyl protecting group R11 with samarium (II) iodide for the reductive cleavage of the sulfonimidoyl-alkyl bond, and optionally cleaving off any protecting groups in compounds of Formula Ia, and optionally reacting the optionally released NH group in the 1-position of the cyclic parent structure with a reagent capable of N-alkylation or a reagent capable of amide formation or blocking the released NH group with an amino protecting group, thereby obtaining said compound corresponding to Formula I.

2. A process for stereochemically controlled production of a compound corresponding to formula I:

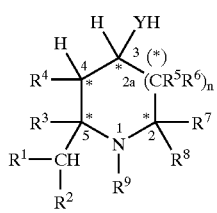

wherein the $R^1R^2CH$ group in the 5-position of the cyclic parent structure and the hydroxy group in the 3-position of the cyclic parent structure are each in the trans position relative to each other and wherein the substituent $R^4$ in the 4-position and the hydroxy group in the 3-position of the cyclic parent structure are each in the cis position relative to each other, and wherein n is 0 or 1, $R^1$ is hydrogen;

$R^2$ is hydrogen;

$R^3$ is hydrogen, and $R^4$ is hydrogen or lower alkyl, or $R^3$ and $R^4$ also together are a $C_3$–$C_6$-alkylene chain optionally containing 1 to 3 double bonds or together form the 7,7-dimethylbicyclo[3.1.1]heptyl-system $R^5$ is hydrogen or lower alkyl, and $R^6$ is hydrogen, and $R^7$ is hydrogen, and $R^8$ is hydrogen;
a monocyclic or bicyclic ring system selected from the group consisting of cyclopropyl, cyclopentyl cyclohexyl, phenyl, p-bromophenyl and 3-indolyl;
lower alkyl; phenyl-lower alkyl or lower-alkoxy lower alkyl, or $R^6$ and $R^7$ also together may form a bond, and $R^5$ and $R^8$, together with the carbon atoms to which they are bonded, may form an aromatic $C^6$-ring system, $R^9$ is lower alkyl: phenyl-lower alkyl optionally substituted one to three times in the phenyl ring by lower alkyl, lower haloalkyl, lower alkoxy or lower haloalkoxy; or an amino protecting group, or $R^8$ and $R^9$ also together may form a $C_3$–$C_4$-alkylene chain, and Y is oxygen or an acid addition salt thereof, wherein any reactive groups which may be present in said compound of Formula I may be blocked by suitable protecting groups, said process comprising the steps of:

a) reacting a compound corresponding to formula II:

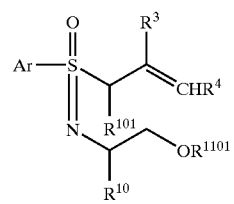

wherein
$R^3$ and $R^4$ have the above meanings, $R^{101}$ has the meaning given above for $R^1$ Ar represents phenyl optionally substituted one to three times by lower alkyl, $R^{10}$ is lower alkyl, or phenyl optionally substituted once in the phenyl ring by lower alkyl or by hydroxy protected with a suitable protecting group, or phenyl-lower alkyl optionally substituted once in the phenyl ring by lower alkyl, and $R^{1101}$ stands for a silyl protecting group, successively with
(i) a base for the deprotonation thereof,
(ii) an organometallic reagent corresponding to the formula VII:

$$XM^2(OR^{12})_3 \quad \text{VII}$$

wherein
X is halogen,
$M^2$ is a tetravalent transition metal, and
$R^{12}$ is lower alkyl, phenyl or phenyl-lower alkyl, and
(iii) a stereoisomer of a compound of the general formula VIII:

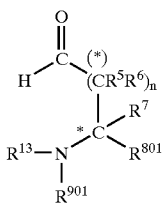

VIII wherein
$R^5$, $R^6$, $R^7$ and n have the above meanings,
$R^{801}$ has the meaning of $R^8$, with any reactive groups, if necessary, being blocked by base-stable protecting groups,
$R^{901}$ together with $R^{801}$ forms a $C_3$–$C_4$-alkylene chain, and
$R^{13}$ is a base-labile amino protecting group which when cleaved leaves behind a nitrogen nucleophile,
to form a stereoisomer of a compound corresponding to the formula IX:

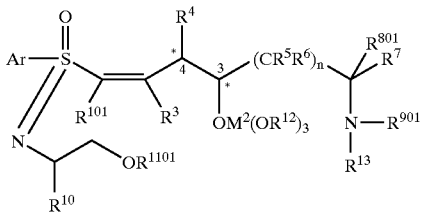

IX wherein
$R^{101}$, $R^3$, $R^4$, $R^5$, $R^6$, $R^7$, $R^{801}$, $R^{901}$, $R^{10}$, $R^{1101}$, $R^{12}$, $R^{13}$, n, Ar and M2 have the above meanings, and
c) converting the compound of Formula IX by treatment with a base reagent for removing the group $R^{13}$, into a compound corresponding to formula Xa:

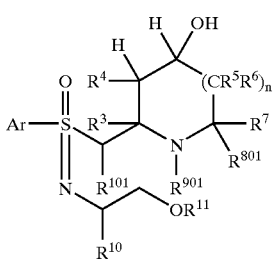

Xa wherein
$R^{101}$, $R^2$, $R^3$, $R^4$, $R^5$, $R^6$, $R^7$, $R^{801}$, $R^{901}$, $R^{10}$, n and Ar have the above meanings, and $R^{11}$ is hydrogen or a silyl protecting group, and cleaving off any silyl protecting group $R^{11}$ which may still be present; and c) for the production of a compound corresponding to formula Ia:

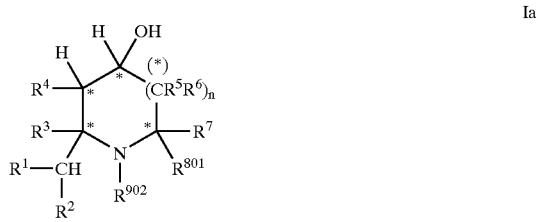

Ia wherein
$R^1$, $R^2$, $R^3$, $R^4$, $R^5$, $R^6$, $R^7$, $R^{801}$ and n have the above meanings, and
$R^{902}$ stands for a base-stable protecting group or, together with $R^{801}$, for a $C_3$–$C_4$-alkylene chain,
reacting a compound corresponding to formula Xa or a compound produced by cleaving off the silyl protecting group R11 with samarium (II) iodide for the reductive cleavage of the sulfonimidoyl-alkyl bond, and
(a) cleaving any protecting groups which may be present, and
(b) reacting any free NH group in the 1-position of the cyclic parent structure with
(i) a reagent capable of N-alkylation, or
(ii) a reagent capable of amide formation, or
(iii) a reagent which blocks the free NH group with an amino protecting group.

3. A process according to claim 1, wherein said base-labile amino protecting group is a fluoren-9-yl-methyloxy-carbonyl radical.

4. A process according to claim 1, wherein the base reagent is piperidine.

5. A process according to claim 1, wherein toluene is used as a solvent in step a).

6. A process according to claim 1, wherein $R^4$ is other than hydrogen in each of the compounds corresponding to formulas I, Ia, II, IX and Xa.

7. A process according to claim 1, wherein $R^{1101}$ is a tert. butyl-dimethylsilyl protecting group or a trimethylsilyl protecting group.

8. A compound corresponding to formula Xa:

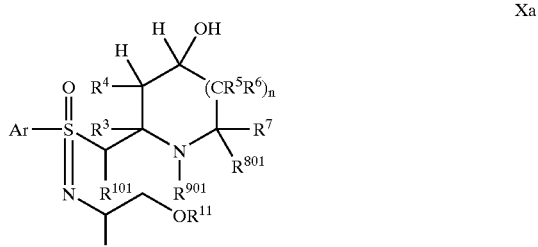

Xa wherein
n is 0 or 1,
$R^3$ is hydrogen, and
$R^4$ is hydrogen or lower alkyl or
$R^3$ and $R^4$ also together are a $C_3$–$C_6$-alkylene chain optionally containing 1 to 3 double bonds or together form the 7,7-dimethyl [3.1.1]heptyl-system $R^5$ is hydrogen or lower alkyl, and
$R^6$ is hydrogen, and
$R^7$ is hydrogen,
$R^{10}$ is lower alkyl, or phenyl optionally substituted once in the phenyl ring by lower alkyl or by hydroxy protected with a suitable protecting group, or phenyl-lower alkyl optionally substituted once in the phenyl ring by lower alkyl,
$R^{11}$ is hydrogen or a silyl protecting group,
$R^{101}$ is hydrogen;
$R^{801}$ is hydrogen;
a monocyclic or bicyclic ring system selected from the group consisting of cyclopropyl, cyclopentyl, cyclohexyl, phenyl, p-bromophenyl and 3-indolyl;
lower alkyl; phenyl-lower alkyl or lower-alkoxy lower alkyl, with the proviso that when n=0, $R^{801}$ is hydrogen,
   a monocyclic or bicyclic ring system selected from the group consisting of cyclopropyl, cyclopentyl, cyclohexyl, phenyl, p-bromophenyl and 3-indolyl;
lower alkyl; or lower-alkoxy lower alkyl, or
$R^6$ and $R^7$ also together may form a bond, and
$R^5$ and $R^{801}$, together with the carbon atoms to which they are bonded, may form an aromatic $C_6$-ring system
$R^{901}$ is hydrogen or together with $R^{801}$ forms a $C_3$–$C_4$-alkylene chain, and
Ar represents phenyl optionally substituted one to three times by lower alkyl,
wherein the sulfur-containing substituent in the 5-position and the hydroxy group in the 3-position of the cyclic parent structure are in the trans position relative to each other, and
wherein the substituent $R^4$ in the 4-position and the hydroxy group in the 3-position of the cyclic parent structure are in the cis position relative to each other, or a compound obtainable by removal of any protecting groups which may be present in said compound corresponding to formula Xa, or an acid addition salt formed with a free amino group which may be present in said compound corresponding to formula Xa.

9. A compound according to claim 8, wherein the cyclic structure of formula Xa contains a secondary nitrogen atom protected by a tert. butoxycarbonyl protecting group.

10. A compound according to claim 8, wherein $R^{801}$ and $R^{901}$ together form a $C_3$–$C_4$-alkylene chain.

11. A method of reductive desulfurisation of an alkyl-sulfonimidoyl compound corresponding to formula Xa of claim 8, wherein $R^3$, $R^4$, $R^5$, $R^6$, $R^7$, $R^{10}$, $R^{11}$, $R^{101}$, $R^{801}$, $R^{901}$ and Ar have the meanings given in claim 8, said method comprising reducing said alkyl-sulfonimidoyl compound with samarium (II) iodide.

12. A process for stereochemically controlled production of an azacyclic compound according to claim 1, wherein the compound of formula II is produced from a compound selected from the group consisting of
(RS)-4(S)-isopropyl-2-p-toluoyl-4,5-dihydro[1,2□6,3]oxathiazol-2-oxide,
(Ss)-4(S)-isopropyl-2-p-toluoyl-4,5-dihydro[1,2□6,3]oxathiazol-2-oxide,
(Rs)-4(R)-isopropyl-2-p-toluoyl-4,5-dihydro[1,2□6,3]oxathiazol-2-oxide, and
(SS)-4(R)-isopropyl-2-p-toluoyl-4,5-dihydro[1,2□6,3]-oxathiazol-2-oxide.

13. A process for stereochemically controlled production of an azacyclic compound according to claim 1, wherein the compound of formula II is produced from [SS,N(1S)]-N-[1-[[tert.-butyldimethylsilyl)-oxy]methyl]-2-methylpropyl]-S-methyl-S-(4-methylphenyl)-sulfoximide or [RS,N(1R)]-N-[1-[[tert.-butyldimethylsilyl)oxy]-methyl]-2-methylpropyl]-S-methyl-S-(4-methylphenyl)sulfoximide.

* * * * *